United States Patent
Sgaravatti et al.

(10) Patent No.: US 12,186,355 B2
(45) Date of Patent: Jan. 7, 2025

(54) **PHYTOCOMPLEX AND SELECTED EXTRACT OF A MERISTEMATIC CELL LINE OF A PLANT BELONGING TO THE GENUS *MELISSA***

(71) Applicant: AETHERA BIOTECH S.R.L., Camisano Vicentino (IT)

(72) Inventors: Elena Sgaravatti, Padua (IT); Giovanna Pressi, Rubano (IT); Flavia Guzzo, Verona (IT)

(73) Assignee: AETHERA BIOTECH S.R.L. (IT)

( * ) Notice: Subject to any disclaimer, the term of this patent is extended or adjusted under 35 U.S.C. 154(b) by 604 days.

(21) Appl. No.: 17/441,259

(22) PCT Filed: Mar. 20, 2020

(86) PCT No.: PCT/IB2020/052589
§ 371 (c)(1),
(2) Date: Sep. 20, 2021

(87) PCT Pub. No.: WO2020/188534
PCT Pub. Date: Sep. 24, 2020

(65) Prior Publication Data
US 2022/0339232 A1  Oct. 27, 2022

(30) Foreign Application Priority Data
Mar. 21, 2019 (IT) .......... 102019000004113

(51) Int. Cl.
| | | |
|---|---|---|
| *A61K 36/53* | (2006.01) | |
| *A01H 5/00* | (2018.01) | |
| *A01H 6/50* | (2018.01) | |
| *A61K 8/99* | (2017.01) | |
| *A61Q 19/08* | (2006.01) | |

(52) U.S. Cl.
CPC .............. *A61K 36/53* (2013.01); *A01H 5/00* (2013.01); *A01H 6/50* (2018.05); *A61K 8/99* (2013.01); *A61Q 19/08* (2013.01)

(58) Field of Classification Search
CPC ................ A61K 36/53; A01H 4/002
See application file for complete search history.

(56) References Cited

FOREIGN PATENT DOCUMENTS

DE  3247610 A1  12/1982

OTHER PUBLICATIONS

International Search Report and Written Opinion for PCT/IB2020/052589, mailed Aug. 3, 2020.
Weitzel et al.: "Cloning and characterisation of rosmarinic acid synthase from Melissa officinalis L", Phytochemisty, Pergamon Press, GB, Jun. 1, 2011, p. 572-573; figure 2 p. 576.
Tonelli et al.: "Ozone-elicited secondary metabolites in shoot cultures of *Melissa officinalis* L", Plant Cell, Tissue and Organ Culture, Springer, NL, vol. 120, No. 2, Sep. 27, 2014, pp. 617-629.
Meftahizade et al.: "Optimization of micropropagation and establishment of cell suspension culture in *Melissa officinalis* L.", African Journal of Biotechnology, vol. 9, No. 28, Jul. 2010, pp. 4314-4321.
Brendler et al.: "Lemon balm (*Melissa officinalis* L.): An evidence-based systematic review by the natural standard research collaboration", Journal of Herbal Pharmacotherapy, Haworth Herbal Press, Binghamton, US, vol. 5, No. 4, Jan. 1, 2005, pp. 71-114, 8, 9, 13-16.
Moradkhani et al.: "*Melissa officinalis* L., a valuable medicine plant: A review", Journal of Medicinal Plants Research, vol. 4, No. 25, Dec. 1, 2010, pp. 2753-2759.
Petersen et al.: "Two New Enzymes of Rosmarinic Acid Biosynthesis from Cell Cultures of Coleus blumei: Hydroxyphenylpyruvate Reductase and Rosmarinic Acid Synthase", Zeitschrift Fuer Naturforschung. C, A Journal of Biosciences., vol. 43, No. 7-8, Aug. 1, 1988, pp. 501-504.

*Primary Examiner* — Qiuwen Mi
(74) *Attorney, Agent, or Firm* — Procopio, Cory, Hargreaves & Savitch LLP; Brent A. Johnson; Erica A. Spence

(57) ABSTRACT

The present invention relates to a meristematic cell line selected from tissue, preferably from callus tissue, of a plant belonging to the genus *Melissa*. The invention also relates to a derivative of the selected cell line, i.e. a phytocomplex or an extract of the cell line. The selected meristematic cell line is characterized by a high rosmarinic acid content.
Furthermore, the present invention relates to the cosmetic, nutraceutical and medical use of the selected meristematic cell line or a derivative thereof.

23 Claims, 13 Drawing Sheets

Fig.2
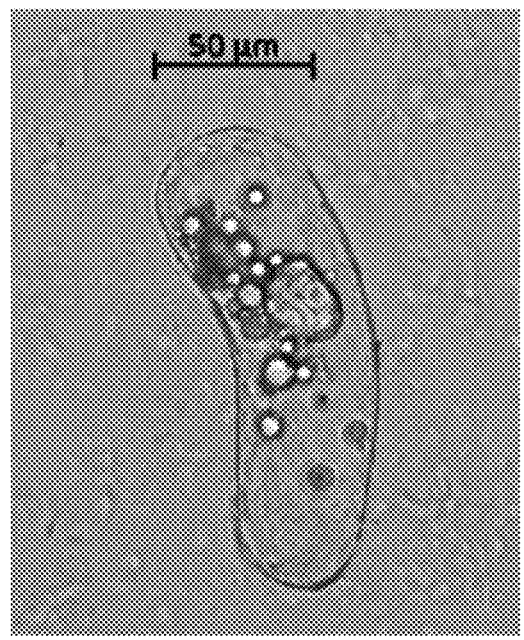
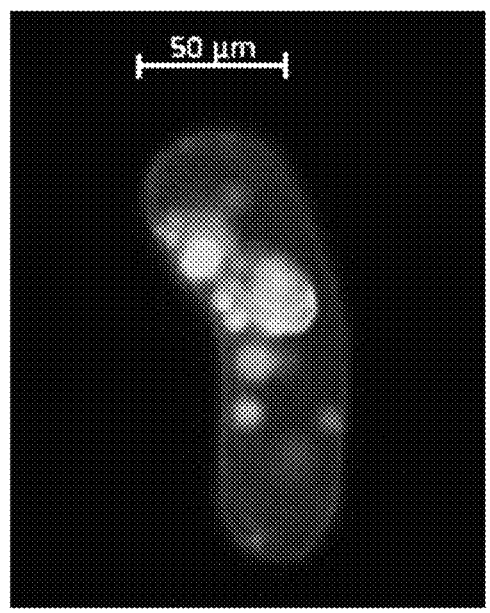
Fig.3

Fig.10

Negative ionization mode

A)

| id | m/z(-) | rt | |
|---|---|---|---|
| 5 | 340,9745 | 2,5281353 | Sucrose |
| 6 | 356,9012 | 20,093431 | |
| 7 | 358,94255 | 24,689271 | rosmarinic acid |
| 8 | 359,82481 | 24,703386 | rosmarinic acid adduct |
| 9 | 360,87429 | 24,71737 | rosmarinic acid adduct |
| 10 | 376,93565 | 2,6421844 | Sucrose |
| 11 | 386,95335 | 2,5354264 | sucrose adduct |
| 12 | 394,8623 | 24,745464 | rosmarinic acid adduct |
| 13 | 403,9077 | 2,7145265 | |
| 14 | 455,25669 | 38,214872 | |
| 16 | 476,97805 | 23,153621 | |
| 19 | 718,94074 | 24,717326 | rosmarinic acid adduct |
| 20 | 719,83626 | 24,703267 | rosmarinic acid adduct |
| 26 | 460,89211 | 24,915272 | |
| 28 | 520,89263 | 23,454071 | |
| 34 | 160,74703 | 2,5713843 | |
| 35 | 178,81698 | 2,5852319 | sucrose fragment |
| 36 | 190,80318 | 2,6641237 | |
| 41 | 438,91665 | 25,116013 | rosmarinic acid sulphate |
| 42 | 444,97009 | 24,529097 | |
| 44 | 450,96943 | 23,123709 | |
| 45 | 502,92855 | 2,5567355 | |
| 46 | 532,85256 | 2,5994299 | |
| 47 | 538,89803 | 2,5856795 | |
| 48 | 548,77136 | 2,5067985 | |
| 49 | 664,95851 | 2,5242749 | |
| 54 | 536,93447 | 25,68588 | |
| 55 | 538,88282 | 22,41893 | |
| 61 | 720,57692 | 24,703386 | rosmarinic acid adduct |
| 62 | 740,96241 | 24,745407 | |

Positive ionization mode

| id | m/z(−) | rt | id | m/z(−) | rt |
|---|---|---|---|---|---|
| 1 | 111,30 | 36,887427 | 36 | 495,40 | 35,373716 |
| 2 | 158,27 | 28,741262 | 37 | 513,46 | 35,436457 |
| 3 | 163,16 | 24,722948 | 38 | 532,46 | 34,43582 |
| 4 | 203,18 | 2,5409646 | 39 | 576,47 | 34,386811 |
| 5 | 212,14 | 27,173636 | 40 | 600,53 | 35,227176 |
| 6 | 228,34 | 37,124607 | 41 | 601,53 | 35,241097 |
| 7 | 230,36 | 30,786278 | 42 | 620,49 | 34,281454 |
| 8 | 254,36 | 37,564464 | 43 | 634,53 | 36,155015 |
| 9 | 274,40 | 29,545516 | 44 | 644,55 | 35,157255 |
| 10 | 275,39 | 29,538463 | 45 | 688,60 | 35,073326 |
| 11 | 279,28 | 35,248107 | 46 | 776,66 | 34,982302 |
| 12 | 280,40 | 38,429403 | 47 | 130,21 | 2,6436309 |
| 13 | 282,41 | 41,567775 | 48 | 147,20 | 2,5990725 |
| 14 | 283,39 | 41,574771 | 49 | 268,39 | 39,433672 |
| 15 | 309,36 | 36,887452 | 50 | 343,20 | 24,708866 |
| 16 | 343,40 | 30,25745 | 51 | 381,18 | 2,5548019 |
| 17 | 365,22 | 2,5837048 | 52 | 383,22 | 24,715881 |
| 18 | 380,42 | 35,610722 | 53 | 469,44 | 35,478398 |
| 19 | 411,24 | 16,242145 | 54 | 590,51 | 36,189856 |
| 20 | 415,30 | 30,849591 | 55 | 664,55 | 34,246391 |
| 21 | 422,38 | 38,017817 | 56 | 144,20 | 2,8096933 |
| 22 | 425,42 | 35,513209 | 57 | 266,23 | 2,5547232 |
| 23 | 429,45 | 35,555017 | 58 | 288,41 | 30,41956 |
| 24 | 444,41 | 34,5765 | 59 | 294,27 | 3,2926022 |
| 25 | 445,40 | 34,576349 | 60 | 342,29 | 2,604765 |
| 26 | 449,43 | 34,569376 | 61 | 447,21 | 24,519459 |
| 27 | 451,39 | 35,457432 | 62 | 341,27 | 25,762928 |
| 28 | 463,19 | 24,906577 | 63 | 413,35 | 38,038643 |
| 29 | 471,42 | 34,562298 | 64 | 533,46 | 34,45704 |
| 30 | 472,31 | 39,824282 | 65 | 399,19 | 24,722885 |
| 31 | 473,45 | 35,478293 | 66 | 213,20 | 27,10229 |
| 32 | 479,20 | 23,395734 | 67 | 219,13 | 2,5407188 |
| 33 | 488,44 | 34,513279 | 68 | 318,42 | 29,615829 |
| 34 | 489,42 | 34,527203 | 69 | 164,19 | 24,736927 |
| 35 | 493,41 | 34,498988 | 70 | 265,23 | 2,4472223 |

Fig.17
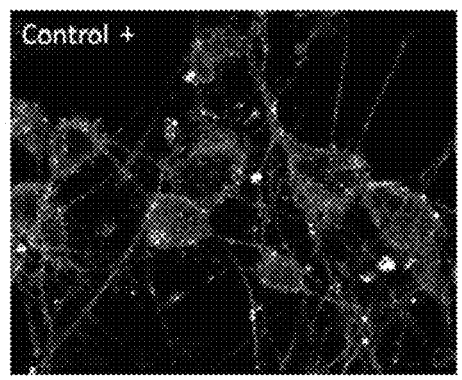
A)
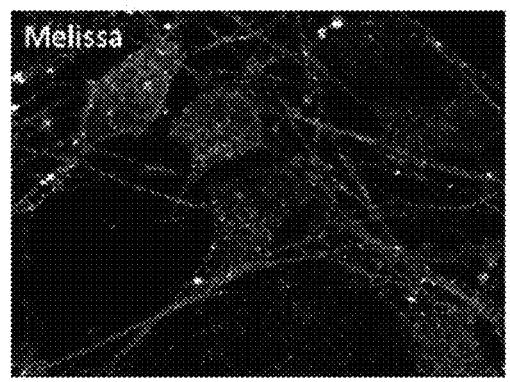
B)
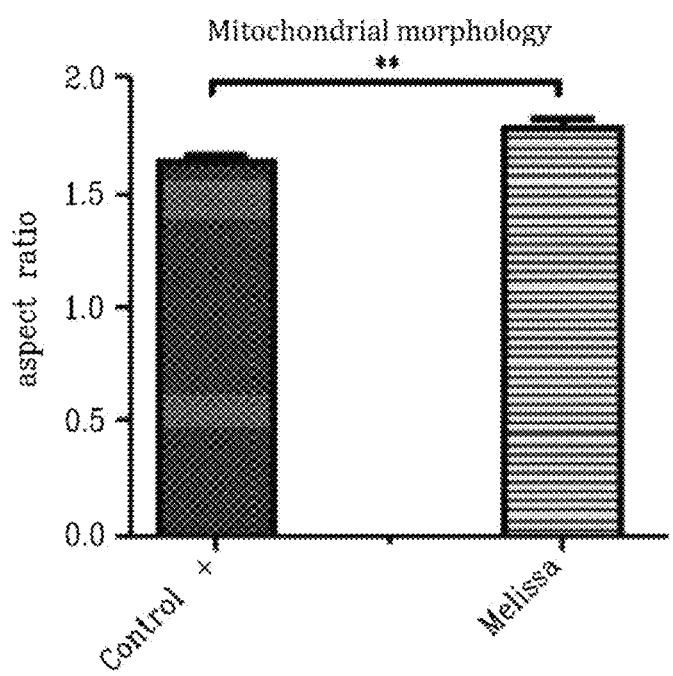
Fig.18

PHYTOCOMPLEX AND SELECTED EXTRACT OF A MERISTEMATIC CELL LINE OF A PLANT BELONGING TO THE GENUS *MELISSA*

CROSS-REFERENCE TO RELATED APPLICATIONS

This application is a national phase application of PCT/IB2020/052589, filed on Mar. 20, 2020, which claims the benefit of Italian Patent Application No. 102019000004113, filed on Mar. 21, 2019, both of which are incorporated by reference herein in their entirety.

FIELD OF THE INVENTION

The present invention relates to a selected meristematic cell line from a plant belonging to the genus *Melissa*, characterized by a high rosmarinic acid content and the cosmetic, nutraceutical and medical use of said meristematic cell line or a derivative thereof.

PRIOR ART

*Melissa officinalis* is a spontaneous, perennial, hardy herbaceous plant that belongs to the Lamiaceae family, is known for its medicinal properties and is highly appreciated as an aromatic herb.

Numerous plants of the Lamiaceae family, used in traditional medicine, have biological activities tied mainly to their polyphenol content and especially their rosmarinic acid content.

Polyphenols, and rosmarinic acid in particular, are typical constituents of *Melissa officinalis*. Numerous data reported in the literature describe the many different activities of rosmarinic acid: antioxidant, antibacterial, antiviral, anti-inflammatory, antiallergic, antithrombotic and antitumour. Furthermore, rosmarinic acid reduces the neurotoxicity induced by β-amyloid proteins, which are found in extracellular vascular and parenchymatic amyloid deposits in people with Alzheimer's disease.

The rosmarinic acid and polyphenol content in these plants is highly variable. This variability is associated with multiple factors, which are difficult to control: seasons, plant age, geographical growing areas and tissues used for the preparation of products.

Furthermore, the preparation of standardized plant derivatives, i.e. with a reproducible content of metabolites, poses numerous problems: variability of the content of the metabolites in different plant tissues, seasonal variability, contaminations by plant parasites, differences tied to the geographical growing areas and loss of the biological activity of the molecule during harvest, storage and extraction. The extreme variability in the content of phytoconstituents of plant preparations obtained directly from a plant, or parts thereof, by extraction negatively impacts the effectiveness of the same.

An alternative method for obtaining contaminant-free standardized plant phytocomplexes in industrial quantities is to use in vitro cell cultures. This technology makes it possible to solve the problems tied to the variability of plant extracts, since it provides preparations with a content of active substances that can be reproduced in a standardized manner. The present invention falls in the context of this technological platform and provides a selected meristematic cell line from which a phytocomplex with a standardized, reproducible content of active substances can be derived.

The present invention provides a selected meristematic cell line of a plant belonging to the genus *Melissa* and derivatives thereof with a high rosmarinic acid content.

SUMMARY OF THE INVENTION

A first aspect of the present invention relates to a selected meristematic cell line derived from a plant belonging to the genus *Melissa*, preferably to the species *Melissa officinalis*, the cell line being preferably derived from a callus tissue obtained from the plant itself.

A second aspect of the present invention relates to a derivative of the selected meristematic cell line, i.e. a phytocomplex or an extract of the cell line.

The meristematic cell line and a derivative thereof are characterized by a high rosmarinic acid content.

A third aspect of the invention relates to a composition comprising the selected meristematic cell line or a derivative thereof, in a mixture with excipients that are accepted from a cosmetic and/or pharmaceutical viewpoint.

The Applicant has demonstrated that the selected cell line or a derivative thereof has an antioxidant, anti-inflammatory activity and is capable of reducing cell death by inhibiting autophagy and favouring maintenance of the morphology of mitochondria. In particular, the selected cell line or a derivative thereof is capable of reducing cell death of neurons subjected to an oxidative insult.

Therefore, the selected meristematic cell line or a derivative thereof can be used as an anti-inflammatory, for the treatment or prevention of neurodegenerative pathologies, for example Parkinson's disease and Alzheimer's disease, and for the treatment or prevention of glioblastoma and brain ischaemia.

Furthermore, the invention also relates to a cosmetic use of the selected meristematic cell line or a derivative thereof to protect skin against the signs of aging and to prevent or reduce cellular oxidation.

The subject matter of the present invention further relates to the nutraceutical use of the selected meristematic cell line or a derivative thereof to prevent or reduce oxidative stress and against cellular aging.

Another aspect of the present invention relates to a process for the preparation and selection of plant meristematic cells of *Melissa* with a high rosmarinic acid content.

BRIEF DESCRIPTION OF THE FIGURES

The present invention is described in detail below and illustrated by way of example with reference to the appended figures, in which:

FIG. 2 shows a magnification (200×) of a portion of FIG. 1.

FIG. 3 shows a magnification (200×) of a portion of FIG. 1 after staining with fluorescein diacetate.

FIG. 10 shows the matrixes in the negative ionization mode (A) and the positive ionization mode (B) (m/Z-=mass negative charge, and m/Z+=mass positive charge and rt=retention time).

FIG. 17 shows dopaminergic neurons treated with rotenone and marked with anti-LC3 antibody, not treated with the Mo-4AR phytocomplex (A) and treated with the Mo-4AR phytocomplex (B).

FIG. 18 shows an evaluation of mitochondrial morphology on dopaminergic neurons treated with rotenone, with and without treatment with the Mo-4AR phytocomplex.

DEFINITIONS

Figure 1:
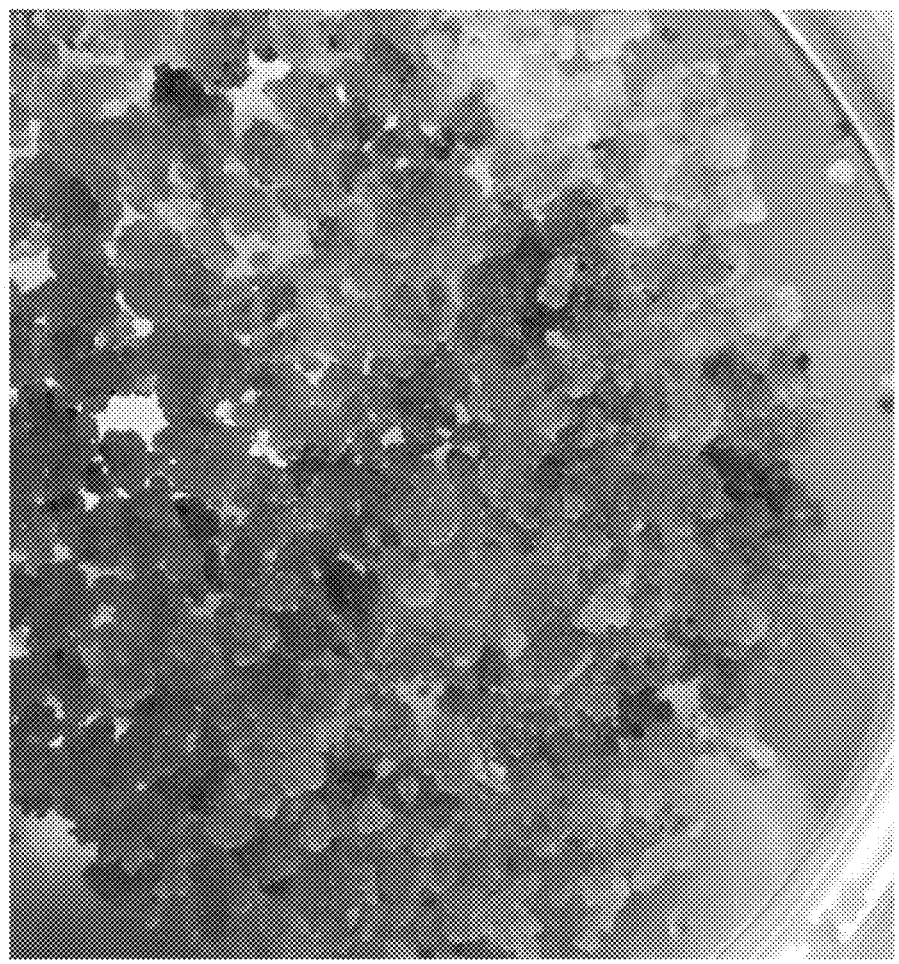
FIG. 1 shows a photo, taken with a bright-field optical microscope, of a selected meristematic cell line according to the present invention, called Mo-4AR, maintained in a solid medium.

In the context of the present invention "meristematic line" or "meristematic cell" means a plant line or cell capable of maintaining the ability to divide by mitosis so as to originate new cells. Every meristematic cell derives from another meristematic cell. The function of plant meristematic cells is comparable to that of the stem cells in animals.

In the context of the present invention, "callus tissue" means a disorganized mass of undifferentiated or very scarcely specialized cells with thin cell walls and a large vacuole where secondary metabolites are accumulated.

In the context of the present invention, unless specified otherwise, "w/w" means a weight/weight amount relative to the dry mass of the cell line.

DETAILED DESCRIPTION OF THE INVENTION

A first aspect of the present invention relates to a meristematic cell line derived from a plant belonging to the genus *Melissa*, preferably to the species *Melissa officinalis*.

In one embodiment, said meristematic cell line is obtained by means of a process comprising the steps of:
1) plating a tissue obtained from a plant belonging to the genus *Melissa* onto a solid culture medium;
2) isolating a plurality of cellular clones;
3) inoculating each of the isolated clones into a liquid culture medium;
4) determining the rosmarinic acid and, preferably, polysaccharide content for each clone;
5) selecting the cellular clone with the highest rosmarinic acid content and, preferably, polysaccharide content.

In step 1), the tissue obtained from a plant of the genus *Melissa* is placed in a solid medium in order to obtain an undifferentiated callus tissue. The tissue of *Melissa* is preferably at least one leaf of *Melissa* or a plurality of leaves of *Melissa*.

In a preferred embodiment of the invention, the solid and liquid culture media comprise salts suitable for the growth of plant cells, sucrose, naphthylacetic acid (NAA),), indoleacetic acid (IAA) and kinetin.

The solid culture media further comprises agar, whereas the liquid culture media does not contain agar.

The solid and liquid culture media each comprise sucrose in a concentration comprised from 15 to 50 g/L preferably from 18 to 45 g/L, naphthylacetic acid (NAA) in a concentration comprised from 0.1 to 2.5 mg/L, preferably from 0.5 to 2 mg/L, indoleacetic acid (IAA) in a concentration comprised from 0.1 to 2.5 mg/L, preferably from 0.3 to 1 mg/L, and kinetin in a concentration comprised from 0.1 mg/L to 2 mg/L preferably from 0.2 mg/L to 1 mg/L.

In a preferred embodiment, the solid culture medium comprises: sucrose in a concentration of from 10 to 30 g/L, preferably from 15 to 25 g/L, naphthaleneacetic acid (NAA) in a concentration of from 0.1 to 2 mg/L, preferably from 0.5 to 1.5 mg/L, indoleacetic acid (IAA) in a concentration of from 0.1 to 2 mg/L, preferably from 0.5 to 1.5 mg/L, and kinetin in a concentration of from 0.2 mg/L to 1 mg/L, preferably from 0.3 mg/L to 0.8 mg/L.

In a preferred embodiment, the liquid culture medium comprises: sucrose in a concentration of from 25 to 50 g/L, preferably from 30 to 45 g/L, naphthaleneacetic acid (NAA) in a concentration of from 0.1 to 2 mg/L, preferably from 0.5 to 1.5 mg/L, indoleacetic acid (IAA) in a concentration of from 0.1 to 2 mg/L, preferably from 0.5 to 1.5 mg/L, and kinetin in a concentration of from 0.2 mg/L to 1 mg/L, preferably from 0.3 mg/L to 0.8 mg/L.

In both the solid and liquid culture media, the salts suitable for the growth of plant cells are selected from: $CaCl_2$, $KNO_3$, $MgSO_4$, $NaH_2PO_4$, $(NH_4)_2SO_4$ and combinations thereof.

In both the solid and liquid culture media, the salts suitable for the growth of plant cells are preferably selected from: $CoCl_2.6H_2O$, $CuSO_4.5H_2O$, $NaEDTA.2H_2O$, $FeSO_4.7H_2O$, $H_3BO_3$, KI, $MnSO_4.H_2O$, $Na_2MoO_4.2H_2O$, $ZnSO_4.7H_2O$ and combinations thereof.

Both the solid and liquid culture media further comprise vitamins suitable for the growth of plant cells, preferably selected from: myo-inositol, nicotinic acid, pyridoxine-HCl, thiamine-HCl and combinations thereof.

In one embodiment, in both the solid and liquid culture media, the salts suitable for the growth of plant cells are selected from: $CaCl_2$), $KNO_3$, $MgSO_4$, $NaH_2PO_4$, $(NH_4)_2SO_4$, $CoCl_2.6H_2O$, $CuSO_4.5H_2O$, $NaEDTA.2H_2O$, $FeSO_4.7H_2O$ $H_3BO_3$, KI, $MnSO_4.H_2O$, $Na_2MoO_4.2H_2O$, $ZnSO_4.7H_2O$ and combinations thereof. This combination of compounds is the medium Gamborg B5.

In one embodiment, both the solid and liquid culture media, in addition to the salts specified above, further comprise vitamins suitable for the growth of plant cells selected from: myo-inositol, nicotinic acid, pyridoxine-HCl thiamine-HCl and combinations thereof.

The solid and liquid culture media preferably each comprise $CaCl_2$) in a concentration comprised from 120 to 170 mg/L, preferably from 130 to 160 mg/L; $KNO_3$ in a concentration comprised from 800 to 3000 mg/L, preferably from 1000 to 2600 mg/L; $MgSO_4$ in a concentration comprised from 220 to 270 mg/L, preferably from 230 to 260 mg/L; $NaH_2PO_4$ in a concentration comprised from 100 to 180 mg/L, preferably from 110 to 150 mg/L; and $(NH_4)_2SO_4$ in a concentration comprised from 100 to 180 mg/L, preferably from 110 to 150 mg/L.

The solid and liquid culture media preferably each comprise $CoCl_2.6H_2O$ in a concentration comprised from 0.01 to 0.05 mg/L, preferably from 0.015 to 0.03 mg/L; $CuSO_4.5H_2O$ in a concentration comprised from 0.01 to 0.05 mg/L, preferably from 0.015 to 0.03 mg/L; $NaEDTA.2H_2O$ in a concentration comprised from 20 to 60 mg/L, preferably from 30 to 45 mg/L; $FeSO_4.7H_2O$ in a concentration comprised from 15 to 45 mg/L, preferably from 20 to 35 mg/L; $H_3BO_3$ in a concentration comprised from 1 to 7 mg/L, preferably from 2 to 5 mg/l; KI in a concentration comprised from 0.1 to 2 mg/L, preferably from 0.4 to 1 mg/L; $MnSO_4.H_2O$ in a concentration comprised from 5 to 20 mg/L, preferably from 7 to 15 mg/L; $Na_2MoO_4.2H_2O$ in a concentration comprised from 0.1 to 0.5 mg/L, preferably from 0.15 to 0.3 mg/L and $ZnSO_4.7H_2O$ in a concentration comprised from 0.5 to 5 mg/L, preferably from 1 to 3 mg/L.

Both the solid and liquid culture media preferably each comprise myo-inositol in a concentration comprised from 70 to 130 mg, preferably from 90 to 110 mg; pyridoxine-HCl from 70 to 130 mg, preferably from 90 to 110 mg; and thiamine-HCl from 5 to 20 mg/L, preferably from 7 to 15 mg/L.

After step 1), the callus tissue is preferably divided into a plurality of portions that are stabilized through successive transfers into the solid culture medium (step 1a)), so as to obtain stabilized cells. This step takes the name of stabilization step.

After the stabilization step 1a), the portions of stabilized cells preferably undergo a first "clonal selection". The clonal selection consists in culturing the stabilized cells for an adequate duration, preferably 5 to 20 days of culture, more preferably 10 to 15 days (step 1 b). The cells are incubated in the dark at a temperature comprised from 15° C. to 35° C., preferably from 24° C. to 26° C.

In step 2), a plurality of cellular clones is isolated by taking aggregates of stabilized cells from the solid culture medium.

In step 3) the cellular clones are each inoculated into the liquid culture medium described above.

According to one embodiment, after a phase of growth for a time such as to obtain an appropriate multiplication of the cellular clone, preferably 10 to 15 days, in step 4) the polysaccharide content of each clone is determined.

In one embodiment, in step 5) a second clonal selection is repeated until obtaining a plant cell line of *Melissa* wherein the production of rosmarinic acid is optimal.

In a preferred embodiment, the clonal selection of step 5) is repeated until obtaining a cell line that comprises an amount of rosmarinic acid greater than 0.05% w/w, preferably comprised from 0.05% to 40% w/w, more preferably comprised from 0.08% to 35% w/w, even more preferably comprised from 3 to 20% w/w.

In a preferred embodiment, said cell line comprises an amount of polysaccharides comprised from 25% to 70% w/w, more preferably comprised from 30% to 65% w/w.

In a preferred embodiment, the cell line comprises an amount of proteins comprised from 1% to 35% w/w, preferably comprised from 1.5% to 30% w/w, more preferably comprised from 2% to 25% w/w.

In a preferred embodiment, the cell line comprises an amount of lipids comprised from 5% to 25% w/w, preferably comprised from 7% to 20% w/w, more preferably comprised from 8% to 18% w/w.

In a preferred embodiment, said selected meristematic cell line is the line Mo-4AR and comprises from 3 to 20% w/w, preferably 3.9-4.2% w/w of rosmarinic acid.

A second aspect of the present invention relates to a derivative of the cell line which is a phytocomplex or an extract of the selected meristematic cell line.

Phytocomplex means: dried or lyophilized cells, a cellular homogenate, or the cell walls and the components thereof. The phytocomplex is preferably a cellular homogenate.

Said phytocomplex preferably comprises an amount of rosmarinic acid greater than 0.05% w/w, preferably comprised from 0.05% to 40% w/w, more preferably comprised from 0.08% to 35% w/w, even more preferably comprised from 3 to 20% w/w relative to the dry mass of the phytocomplex.

The phytocomplex also comprises an amount of polysaccharides comprised from 25% to 70% w/w, more preferably comprised from 30% to 65% p/p relative to the dry mass of the phytocomplex.

The phytocomplex comprises an amount of proteins comprised from 1% to 35% w/w, preferably comprised from 1.5% to 30% w/w, more preferably comprised from 2% to 25% w/w relative to the dry mass of the phytocomplex.

The phytocomplex further comprises an amount of lipids comprised from 5% to 25% w/w, preferably comprised from 7% to 20% w/w, more preferably comprised from 8% to 18% w/w relative to the dry mass of the phytocomplex.

In a preferred embodiment, said phytocomplex is derived from said selected meristematic cell line Mo-4AR and comprises from 3 to 20% w/w preferably 3.9-4.2% w/w of rosmarinic acid. The phytocomplex is preferably a cellular homogenate of the selected meristematic cell line Mo-4AR.

Extract means an extract in an alcoholic solvent, for example in methanol or ethanol, or a water/ethanol mixture in different proportions: 50:50 or 60:40 or 70:30, of the cell line itself or a phytocomplex of the cell line. The extract is preferably an extract of a cellular homogenate of the line. The content of said extract corresponds to the content of the phytocomplex or cell line from which it was derived, with the variability due to the extraction technique.

A third aspect of the present invention relates to a composition comprising the meristematic cell line and/or a derivative thereof (phytocomplex and/or extract) in association with at least one excipient that is accepted from a cosmetic, nutraceutical and/or pharmaceutical viewpoint.

In one embodiment, the composition comprises the cell line and/or a derivative thereof in a concentration comprised from 0.01% to 30% w/w, preferably from 0.03% to 15% w/w, more preferably from 0.05% to 10% w/w relative to the weight of the composition. Said composition preferably comprises a phytocomplex which is a cellular homogenate.

In one embodiment, the cell line and/or a derivative thereof is dispersed before being mixed with the excipients to prepare the composition of the invention. By way of example, suitable dispersing agents are glycerine, propylene glycol or butylene glycol.

The composition of the present invention comprises at least one excipient acceptable for pharmaceutical and/or cosmetic use, which is useful in the preparation of the composition and is generally biologically safe and nontoxic.

Said excipient can be at least one conditioning, humectant, or occlusive agent, a surfactant, a stabilizing agent, a preservative or an emollient for the skin.

The composition of the invention is formulated for oral administration, preferably as a pill, capsule, tablet, granular powder, hard-shelled capsule, orally dissolving granule, sachet or lozenge.

In one embodiment, the composition is formulated to release the active ingredients contained therein rapidly, or in a delayed and/or controlled manner after administration, preferably formulated as a liposome.

According to one embodiment of the invention, the composition is formulated for parenteral administration. In particular, the composition is formulated in liquid form, preferably in the form of a sterile solution, emulsion or suspension.

The composition can also be formulated for topical use as a cream, gel-cream, gel, serum, oil, emulsion, emulsion-gel (emulgel), ointment, eye drops, mouthwash, patch, spray, preferably nasal spray or stick (such as lip balm). The formulation of the composition as a face serum or cream is particularly preferred, preferably as a hand cream or face cream, for example with anti-wrinkle and antioxidant activity.

The experimental data included herein indicate that the cell line or a derivative thereof, as described above, are capable of reducing cell death and exerting an anti-inflammatory effect and an antioxidant effect (reduction of free radicals).

In particular, the Applicant has shown that a derivative of the cell line is capable of limiting cell death in an in vitro neurodegenerative model, in particular in a model of Parkinson's disease, by reducing autophagy and favouring the maintenance of the mitochondrial morphology. The inhibition of autophagy and maintenance of mitochondrial morphology are mechanisms associated with reduced neuron death. In fact, autophagy at low levels in the neurons is a physiological condition for maintaining homeostasis, whereas excessive autophagy can be the cause of neuron death. Moreover, an altered mitochondrial morphology can be correlated to cell damage and, therefore, lead to cell death.

Furthermore, the Applicant has demonstrated that a derivative of the cell line is capable of reducing inflammatory levels by inhibiting the release of interleukin 1-beta (IL-1β), and reducing oxidative stress following an oxidative insult with lipopolysaccharide (LPS).

A further aspect of the present invention relates to the cell line or a derivative thereof for use as a medicament, in particular for the treatment or prevention of neurodegenerative pathologies, for example Parkinson's disease and Alzheimer's disease, and for the treatment or prevention of glioblastoma and brain ischaemia.

The present invention further relates to the cell line or a derivative thereof for use as an anti-inflammatory.

A further aspect of the present invention relates to the cosmetic use of the cell line or of a derivative thereof.

Cosmetic use means the prevention, attenuation and/or combatting of the signs of skin aging, anti-wrinkle activity and antioxidant activity.

A further aspect of the present invention relates to the use of the cell line or a derivative thereof as a dietary supplement for preventing or attenuating or combatting the signs of skin aging and/or the increase in free radicals. In this case, the cell line or a derivative thereof is formulated in compositions for oral use, such as a pill, capsule, tablet, granular powder, hard-shelled capsule, orally dissolving granule, sachet or lozenge.

Another aspect of the present invention relates to a process for the preparation and selection of meristematic plant cells with a high rosmarinic acid content and, preferably, with a high polysaccharide content. Said method comprises the steps of:

1) plating a tissue obtained from a plant belonging to the genus *Melissa* onto a solid culture medium;
2) isolating a plurality of cellular clones;
3) inoculating each of the isolated clones into a liquid culture medium;
4) determining the rosmarinic acid and, preferably, polysaccharide content for each clone;
5) selecting the cellular clone with the highest rosmarinic acid and polysaccharide content, In one embodiment, the preparation of meristematic entails collecting tissue, preferably of leaves from plants selected from the species *Melissa officinalis*, washing it, for example with water, fragmenting it into small pieces and sterilizing it on plates, for example with successive treatments with ethanol, sodium hypochlorite and a mercury salt.

In step 1), the collected tissue is placed in a solid culture medium in order to obtain an undifferentiated callus tissue.

In a preferred embodiment of the invention, the solid and liquid culture media comprise salts suitable for the growth of plant cells, sucrose, naphthylacetic acid (NAA), indoleacetic acid (IAA) and kinetin.

The solid culture media further comprises agar, whereas the liquid culture media does not contain agar.

The solid and liquid culture media preferably each comprise sucrose in a concentration comprised from 15 to 50 g/L more preferably from 18 to 45 g/L, naphthylacetic acid (NAA) in a concentration comprised from 0.1 to 2.5 mg/L, more preferably from 0.5 to 2 mg/L, indoleacetic acid (IAA) in a concentration comprised from 0.1 to 2.5 mg/L, more preferably from 0.3 to 1 mg/L, and kinetin in a concentration comprised from 0.1 mg/L to 2 mg/L preferably from 0.2 mg/L to 1 mg/L.

In a preferred embodiment, the solid culture medium comprises: sucrose in a concentration of from 10 to 30 g/L, preferably from 15 to 25 g/L, naphthaleneacetic acid (NAA) in a concentration of from 0.1 to 2 mg/L, preferably from 0.5 to 1.5 mg/L, indoleacetic acid (IAA) in a concentration of from 0.1 to 2 mg/L, preferably from 0.5 to 1.5 mg/L, and kinetin in a concentration of from 0.2 mg/L to 1 mg/L, preferably from 0.3 mg/L to 0.8 mg/L.

In a preferred embodiment, the liquid culture medium comprises: sucrose in a concentration of from 25 to 50 g/L, preferably from 30 to 45 g/L, naphthaleneacetic acid (NAA) in a concentration of from 0.1 to 2 mg/L, preferably from 0.5 to 1.5 mg/L, indoleacetic acid (IAA) in a concentration of from 0.1 to 2 mg/L, preferably from 0.5 to 1.5 mg/L, and kinetin in a concentration of from 0.2 mg/L to 1 mg/L, preferably from 0.3 mg/L to 0.8 mg/L.

In both the solid and liquid culture media, the salts suitable for the growth of plant cells are selected from: $CaCl_2$), $KNO_3$, $MgSO_4$, $NaH_2PO_4$, $(NH_4)_2SO_4$ and combinations thereof.

In both the solid and liquid culture media, the salts suitable for the growth of plant cells are preferably selected from: $CoCl_2.6H_2O$, $CuSO_4.5H_2O$, $NaEDTA.2H_2O$, $FeSO_4.7H_2O$, $H_3BO_3$, $KI$, $MnSO_4.H_2O$, $Na_2MoO_4.2H_2O$, and $ZnSO_4.7H_2O$ and combinations thereof.

Both the solid and liquid culture media further comprise vitamins suitable for the growth of plant cells, preferably selected from: myo-inositol, nicotinic acid, pyridoxine-HCl, thiamine-HCl and combinations thereof.

In one embodiment, in both the solid and liquid culture media, the salts suitable for the growth of plant cells are selected from: $CaCl_2$), $KNO_3$, $MgSO_4$, $NaH_2PO_4$, $(NH_4)_2SO_4$, $CoCl_2.6H_2O$, $CuSO_4.5H_2O$, $NaEDTA.2H_2O$, $FeSO_4.7H_2O$ $H_3BO_3$, KI, $MnSO_4.H_2O$, $Na_2MoO_4.2H_2O$, $ZnSO_4.7H_2O$ and combinations thereof. This combination of salts is the medium Gamborg B5.

In one embodiment, both the solid and liquid culture media, in addition to the salts specified above, further comprise vitamins suitable for the growth of plant cells selected from: myo-inositol, nicotinic acid, pyridoxine-HCl thiamine-HCl and combinations thereof.

The solid and liquid culture media preferably each comprise $CaCl_2$) in a concentration comprised from 120 to 170 mg/L, more preferably from 130 to 160 mg/L; $KNO_3$ in a concentration comprised from 800 to 3000 mg/L, more preferably from 1000 to 2600 mg/L; $MgSO_4$ in a concentration comprised from 220 to 270 mg/L, more preferably from 230 to 260 mg/L, $NaH_2PO_4$ in a concentration comprised from 100 to 180 mg/L, more preferably from 110 to 150 mg/L; and $(NH_4)_2SO_4$ in a concentration comprised from 100 to 180 mg/L, more preferably from 110 to 150 mg/L.

The solid and liquid culture media preferably each comprise $CoCl_2.6H_2O$ in a concentration comprised from 0.01 to 0.05 mg/L, more preferably from 0.015 to 0.03 mg/L; $CuSO_4.5H_2O$ in a concentration comprised from 0.01 to 0.05 mg/L, more preferably from 0.015 to 0.03 mg/L; $NaEDTA.2H_2O$ in a concentration comprised from 20 to 60 mg/L, more preferably from 30 to 45 mg/L; $FeSO_4.7H_2O$ in a concentration comprised from 15 to 45 mg/L, more preferably from 20 to 35 mg/L; $H_3BO_3$ in a concentration comprised from 1 to 7 mg/L, more preferably from 2 to 5 mg/l; KI in a concentration comprised from 0.1 to 2 mg/L, more preferably from 0.4 to 1 mg/L; $MnSO_4.H_2O$ in a concentration comprised from 5 to 20 mg/L, more preferably from 7 to 15 mg/L; $Na_2MoO_4.2H_2O$ in a concentration comprised from 0.1 to 0.5 mg/L, more preferably from 0.15 to 0.3 mg/L and $ZnSO_4.7H_2O$ in a concentration comprised from 0.5 to 5 mg/L, more preferably from 1 to 3 mg/L.

Both the solid and liquid culture media preferably each comprise myo-inositol in a concentration comprised from 70 to 130 mg, more preferably from 90 to 110 mg; pyridoxine-HCl from 70 to 130 mg, more preferably from 90 to 110 mg; and thiamine-HCl from 5 to 20 mg/L, more preferably from 7 to 15 mg/L.

After step 1), the callus tissue is preferably divided into a plurality of portions that are stabilized through successive transfers into the solid culture medium (step 1a)), so as to obtain stabilized cells. This step takes the name of stabilization step.

After the stabilization step 1a), the stabilized cells preferably undergo a first "clonal selection". The clonal selection consists in culturing the stabilized cells for an adequate duration, preferably 5 to 20 days of culture, more preferably 10 to 15 days (step 1b). The cells are incubated in the dark at a temperature comprised from 15° C. to 35° C., preferably from 24° C. to 26° C.

In step 2), a plurality of cellular clones is isolated by taking aggregates of stabilized cells from the solid culture medium.

In step 3) the cellular clones are each inoculated into the liquid culture medium described above.

According to one embodiment, after a phase of growth for a time such as to obtain an appropriate multiplication of the cellular clone, preferably 10 to 15 days, in step 4) the polysaccharide content of each clone is determined.

In one embodiment, in step 5) a second clonal selection is repeated until obtaining a plant cell line of *Melissa* wherein the production of rosmarinic acid, is optimal.

The selected cell line is then multiplied, in a flask or bioreactor or fermenter, so as to obtain an increase in the biomass. The multiplication of the biomass takes place in a first step in a liquid growth medium called MO. The liquid growth medium MO is a medium containing the Gamborg salts specified above, the vitamins listed above, sucrose, NAA, IAA and kinetin.

The liquid growth medium MO contains, among the Gamborg salts, $KNO_3$ in an amount comprised from 1.5 g/L to 3.5 g/L, preferably from 2 g/L to 3 g/L. Sucrose is preferably comprised from 15 g/L to 25 g/L. NAA is preferably comprised from 0.5 mg/L to 1.5 mg/L. IAA is preferably comprised from 0.2 mg/L and 1 mg/L. Kinetin is preferably comprised from 0.2 mg/L to 1 mg/L.

The cells grown in the liquid medium MO are transferred, for the final phase of growth, into a final liquid medium MO-F containing the Gamborg salts, vitamins, sucrose, NAA, IAA and kinetin, which induces an increase in rosmarinic acid content and biomass.

The final liquid medium MO-F contains, among the Gamborg salts, $KNO_3$ in an amount comprised from 0.5 g/L to 2 g/L. Sucrose is preferably comprised from 25 g/L to 45 g/L. NAA is preferably comprised from 0.2 mg/L to 1 mg/L. IAA is preferably comprised from 0.2 mg/L to 1 mg/L. Kinetin is preferably comprised from 0.1 mg/L to 0.5 mg/L.

According to a preferred embodiment, the growth of the cell line in the flask, bioreactor or fermenter, both in the MO growth medium and in the final MO-F medium, is carried out at a temperature comprised from 15° C. to 35° C., typically about 25° C., for a period comprised from 7 to 30 days, preferably from 14 to 21 days, under conditions of darkness.

At the end of growth in the final liquid medium MO-F, the cell line is filtered and the cells are recovered in order to be used in the subsequent steps in the form of a phytocomplex, or else they may undergo a subsequent extraction phase in an alcohol solvent in order to produce a cell extract characterized by a high rosmarinic acid content.

The phytocomplex can be obtained by lyophilization or drying of live cells; in this case, the phytocomplex is a lyophilizate of dead cells.

In one embodiment, at the end of growth in the flask, bioreactor or fermenter the cells are homogenized, for example by mechanical disintegration, preferably in an acidified solution (for example with ascorbic acid or citric acid or acetic acid) and subsequently lyophilized or dried. In the latter case, the phytocomplex is a cellular homogenate wherein the cells and the internal structures thereof are disintegrated. These different types of phytocomplexes are all characterized in that they have a high rosmarinic acid content as previously described.

Alternatively, the phytocomplex, preferably in the form of a cellular homogenate, undergoes extraction in an alcohol solvent (for example methanol or ethanol or ethanol/water mixtures) using conventional techniques. The extract thus obtained is characterized by a high rosmarinic acid content as detailed above and can be used for the preparation of cosmetic, nutraceutical or pharmaceutical compositions as described above.

Alternatively, the live cells as such, following purification, can be directly employed for the preparation of the compositions of the invention.

EXAMPLES

Generation and Selection of the Line of Meristematic Cells of *Melissa officinalis*

The induction of callus tissue was obtained using standard procedures described in the literature. This procedure provides for the collection of leaves from sterile plants of *Melissa officinalis*. The sterile plants were obtained from seeds sanitized by means of a treatment in sequence with 70% ethanol in water for about 2 minutes, 2% sodium hypochlorite and 0.1% Tween 20 for 15 minutes and, finally, at least 4 washes with sterile distilled water. The sanitized seeds are placed in trays containing nutrient medium Gamborg B5 rendered solid by adding agar and without growth hormones. After a suitable period of incubation under light (15 days) and at 25° C. the seeds begin germinating. Twenty days after germination small leaves are collected from the plants grown under sterile conditions. The leaves are fragmented into small pieces of sub-centimetric dimensions (0.1-0.5 cm). The fragments of plant tissue are deposited in Petri dishes containing nutrient medium rendered solid by adding agar and supplemented with growth hormones. After a suitable period of incubation in the dark at 25° C., an undifferentiated callus tissue forms; it is then multiplied after transfer onto a larger surface with fresh medium.

The meristematic cells obtained are stabilized by means of a certain number of transfers (sub-cultures) onto solid culture media.

The cell line of *Melissa officinalis* is maintained in a Gamborg B5 medium with the addition of 20 g/L of sucrose, 1 mg/L of naphthaleneacetic acid (NAA), 1 mg/L of indoleacetic acid (IAA), 0.5 mg/L of kinetin and 0.7-0.9% plant agar, final pH 6.5 (MO medium). The cell line obtained in this specific culture medium was called Mo-4AR. The belonging of the meristematic cells obtained to the botanical species *Melissa officinalis* was confirmed by DNA fingerprint analysis.

The cell line MO-4AR is multiplied to obtain sufficient amounts of biomass to transfer the cells into the liquid culture medium (MO medium without agar). After growth in the liquid medium, the cell suspensions can be transferred into bioreactors which can contain the final productive medium or the MO growth medium for further phases of growth.

The productive liquid medium (optimized to increase the rosmarinic acid content) is a Gamborg B5 with the addition of 35 g/L of sucrose, 0.5 mg/L of NAA, 0.5 mg/L of IAA and 0.25 mg/L of kinetin, final pH 6.5 (MO-F medium).

Morphological Characteristics of the Cell Line Mo-4AR

The cell line of *Melissa officinalis* called Mo-4AR is maintained in solid MO culture medium, is beige-coloured with brown tinges and has a friable texture. FIGS. 1-3 show photographs of the cell culture maintained in solid MO medium (FIG. 1) and cells of the line Mo-4AR seen under an AXIO-Imager A2 optical microscope (ZEISS), in the bright field mode (FIG. 2) and after staining with fluorescein diacetate (FIG. 3).

Homogenization Procedure

The procedure for homogenizing the biomasses of cells selected and grown in bioreactors for 14 days at 25° C. (±2) comprises the following steps:
a) filtration of the biomass obtained from the growth of the Mo-4AR cell culture in the MO-F culture medium in order to have only cells and discard the medium;
b) washing of the cells with a double volume, relative to the cells, of saline solution (0.9% W/V NaCl in sterile water);
c) addition of 1.5% W/W (from 0.5 to 2% W/W) of citric acid (or ascorbic acid or a mixture of citric and ascorbic acid) to the filtered, washed biomass;
d) homogenization of the mixture, for example with an Ultra-Turrax or any other instrument suitable for breaking down the cells and the internal structures thereof;
e) drying of the biomass by lyophilization or air circulation drying or rotating cylinder drying or fluid bed drying or atomization.

Using the procedure described, one obtains the phytocomplex called Mo-4AR.

Description of the content of the Mo-4AR phytocomplex:
35-55% carbohydrates
0.1-30% rosmarinic acid
2-25% proteins
8-18% lipids
3-6% moisture
5-13% ash
5-30% citric acid Examples of preparation of the standardized Mo-4AR phytocomplex in MO-F medium are provided by way of non-limiting example.

The phytocomplex thus obtained is used as such or dispersed in plant glycerine or butylene glycol or propylene glycol in concentrations ranging from 0.5 to 5% w/w. The suspensions thus obtained are called CROP®-G.

Preparation and Analysis of the Mo-4AR Phytocomplex

Meristematic cells, stabilized and selected as previously described, deriving from the line of *Melissa officinalis* called Mo-4AR, cultured in solid MO medium (Gamborg B5 containing 20 g/L of sucrose, 1 mg/L of naphthaleneacetic acid, 1 mg/L of indoleacetic acid, 0.5 mg/L of kinetin and 0.8% plant agar, final pH 6.5) were inoculated into 5 flasks with a 1-litre capacity, containing 200 ml of liquid MO-F medium (Gamborg B5 with the addition of 35 g/L of sucrose, 0.5 mg/L of NAA, 0.5 mg/L of IAA, 0.25 mg/L of K, final pH 6.5). The amount of meristematic cells inoculated into the liquid medium was equal to 6% W/V. The suspensions thus obtained were incubated in the dark at 25° C. and placed on top of an orbital shaker set on 120 RPM. After 14 days of incubation, the plant biomass (1 litre of cell suspension) was collected and filtered over a nylon mesh with a porosity of 50 μm and washed with 820 ml of sterile saline solution (0.9% W/V). The washed cells (fresh weight 410 g) were supplemented with 4.1 g of citric acid and homogenized with an Ultra-Turrax.

The homogenized cells were lyophilized. 32 g of lyophilizate (Mo-4AR phytocomplex) with a content of rosmarinic acid equal to 1.28 g, total polysaccharides of 16 g, 5.76 g of proteins, 2.72 g of lipids, 1.44 g of ash and 4 g of citric acid were obtained from 1 litre of cell suspension.

TABLE 1

Characterization of the Mo-4AR phytocomplex.

|  | g/32 g Mo-4AR phytocomplex | % w/w |
| --- | --- | --- |
| Rosmarinic acid | 1.28 | 4 |
| Polysaccharides | 16 | 50 |
| Proteins | 5.76 | 18 |
| Lipids | 2.72 | 8.5 |
| Ash | 1.44 | 4.5 |
| Citric acid | 4 | 12.5 |
| Moisture | 0.8 | 2.5 |

The characterization of the homogenate was carried out using the methods described below:

a) Quantification of rosmarinic acid in the Mo-4AR phytocomplex by UPLC-DAD 100 mg of powder of the Mo-4AR phytocomplex were weighed into a 15 mL test tube and 30 volumes of ethanol and water 60:40 (V/V) were added. The suspension was mixed for 30 seconds with a vortex mixer and sonicated for 15 minutes in an ice bath; finally, it was centrifuged at 4000 rpm for 15 minutes at 6° C. At the end of centrifugation, the supernatant was recovered. 15 mL of supernatant were transferred into a new test tube and preserved in ice until loading into the UPLC system. The sample was diluted 1:10 (first 1:5 in a solvent and then 1:2 in water). The diluted sample was filtered over 0.22 prn filters before being loaded into the UPLC system. The chromatography system used for quantification of the rosmarinic acid consists in an Acquity UPLC BEH C18 1.7 μm column, size 2.1×100 mm, coupled to an Acquity UPLC BEH C18 1.7 prn Van-Guard Pre-Column 3/Pk, size 2.1×5 mm. The platform used for the UPLC-DAD analysis comprises a UPLC system (Waters) consisting of an eluent management module, Binary Solvent Manager model I Class, and an auto-sampler, Sample Manager 13 FTN model I Class, coupled to a PDA eλ diode array detector. Empower 3 (Waters) software was used to acquire and analyse the data. The chromatography method used was the following: solvent A: water, 0.1% formic acid; solvent B: 100% acetonitrile. The initial condition is 99% solvent A; moreover, the flow remains constant at 0.350 ml/min throughout the duration of the analysis. The chromatography column was temperature controlled at 30° C. Elution of the molecules was conducted by alternating gradient and isocratic phases, as indicated in Table 2.

TABLE 2

| time from start of the analysis (minutes) | percentage of solvent B | Slope |
|---|---|---|
| 0 | 1% | |
| 1 | 1% | linear |
| 11 | 40% | linear |
| 12 | 100% | linear |
| 13 | 100% | linear |
| 13.10 | 1% | linear |
| 15 | 1% | linear |

Figure 4:
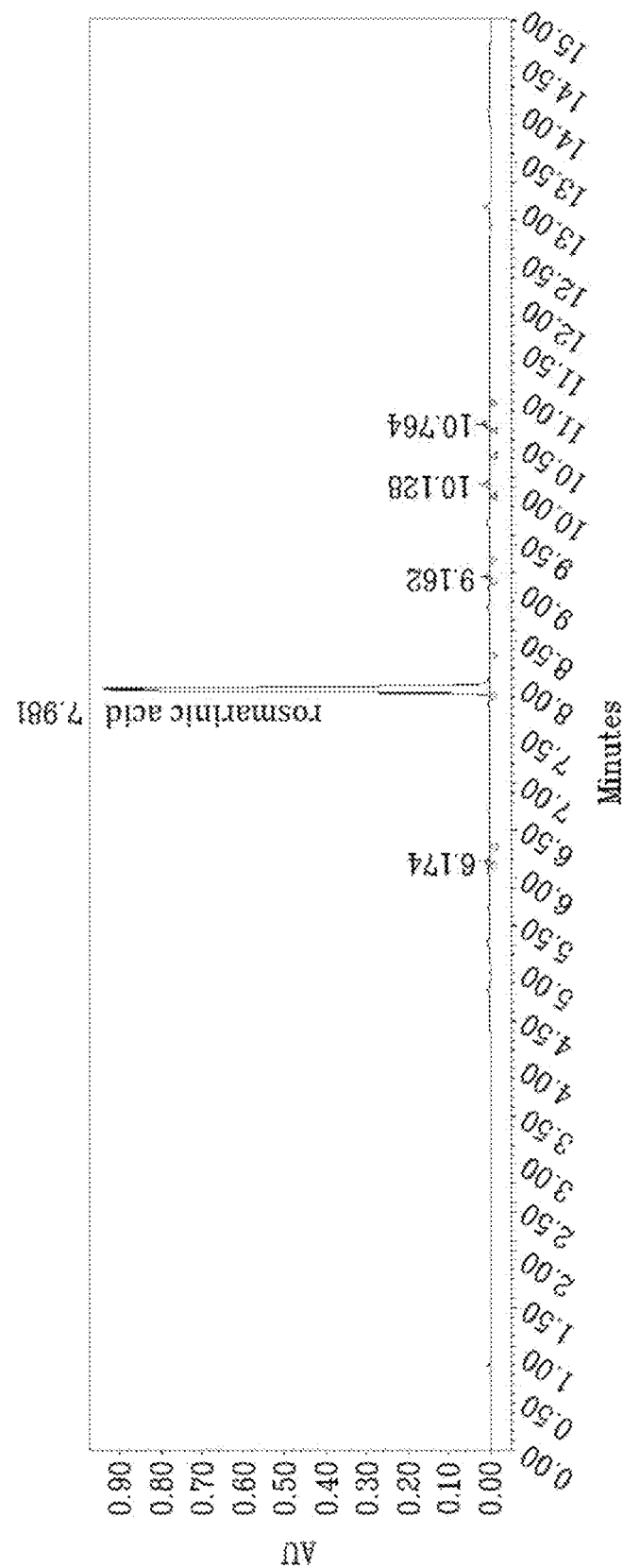
FIG. 4 shows a chromatogram at 330 nm of the Mo-4AR phytocomplex.

For quantification of the rosmarinic acid, the chromatogram associated with the wavelength of 330 nm was used. The rosmarinic acid was quantified thanks to the calibration curve of the authentic commercial standard of rosmarinic acid (CAS 20283-92-5; purity ≥95%; Sigma Aldrich). The data analysis was carried out with Empower 3 software. The chromatographic profile of the Mo-4AR phytocomplex at 330 nm is shown in FIG. 4.

Table 3 shows the concentration of rosmarinic acid detected in the Mo-4AR phytocomplex by UPLC analysis.

TABLE 3

| Extract | % rosmarinic acid |
|---|---|
| Mo-4AR phytocomplex | 4.0 ± 0.05 | b) HPLC-ESI-MS analysis of the Mo-4AR phytocomplex

The powder of the Mo-4AR phytocomplex was extracted with 30 volumes of methanol:water 90:10 for 15 minutes in a sonicator at 40 Hz under ice, after being stirred in a vortex-type mixer for 30 seconds; the extract was recovered after centrifugation at 18000 g for 10 minutes at 4° C. Prior to the analysis, the sample was diluted with suitable amounts of the same solvent (methanol:water 90:10) so as to obtain a spectrophotometric absorbance of between 0.4 and 0.6 at 320 nm. The sample was further diluted with water and analysed by HPLC-ESI-MS.

For the mass spectrometry associated with the chromatographic separation, use was made of an HPLC system (Beckman Coulter System Gold 1, Solvent Module provided with auto-sampler) coupled "on-line" with an Esquire 6000 mass spectrometer (Bruker Daltonik GmbH, Germany), provided with an ESI source. The chromatographic and mass data were collected using the Bruker Daltonics Esquire 5.2-EsquireControl 5.2 program and processed using the Bruker Daltonics Esquire 5.2-Data Analysis 3.2 program (Bruker Daltonik GmbH, Germany).

Flow: 200 μl/min, 25° C.; injection volume: 10 μl.
Column used: Alltima HP C18 3 μm 150×2.1 mm, coupled with a 7.5×2.1 mm guard column (Alltech Associates, Inc, Deerfield, Ill.).
ESI: nebulizer gas N2, pressure 50 psi, temp. 350° C., drying gas 10 l/min
Mass acquisition: Full Scan alternated in the range 50-1500 m/z; vacuum pressure: $1.4 \times 10-5$ mbar.
For the tandem mass spectrometry: fragmentation amplitude: 1 V; collision gas: helium.
The chromatographic separation method used was the following:
Eluents:
  Solution A: 5% ACN and 0.5% formic acid in water,
    Solution B: 100% ACN Total length of the elution: 42 minutes
Gradient:
Start of analysis: eluent A 100%;
gradient 1: 10% of eluent B in 2 minutes;
gradient 2: at 2 minutes, 20% of B in 10 minutes;
gradient 3: at 12 minutes, 25% of B in 2 minutes;
gradient 4: at 14 minutes, 70% of B in 7 minutes;
isocratic 1: with 70% of B for 6 minutes;
gradient 5: at 27 minutes, 90% of B in 5 minutes;
isocratic 2: 90% of B per 10 minutes;
final re-equilibration of column: at 42 minutes, 0% of B in 1 minute, end of analysis at 60 minutes.

Figure 5:
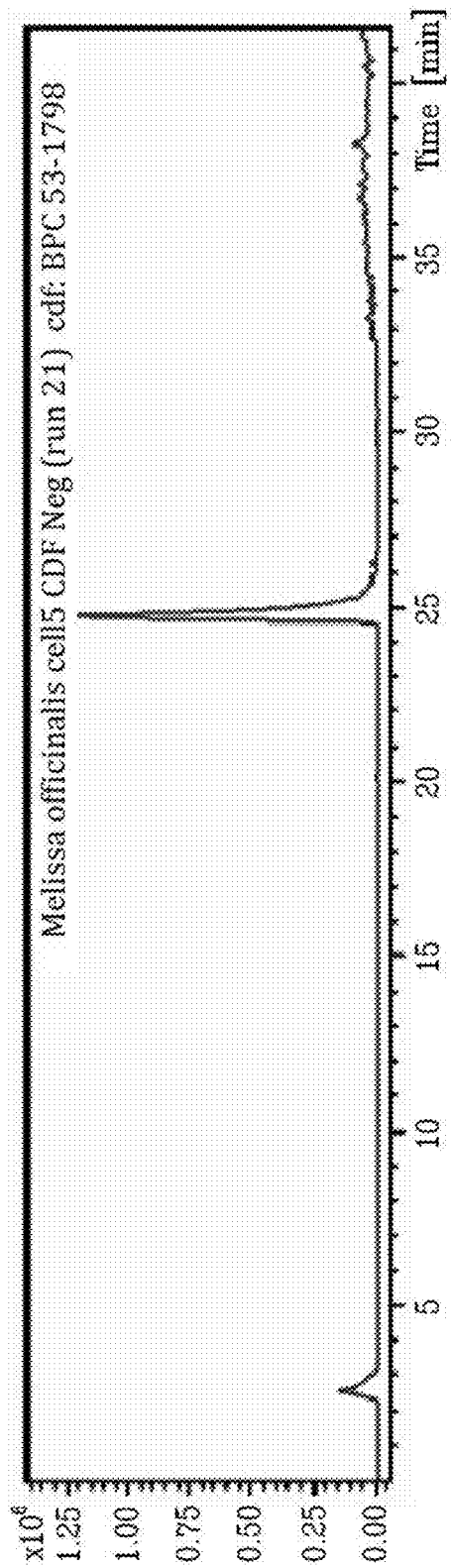
FIG. 5 shows the chromatographic profile of the Mo-4AR phytocomplex obtained by negative ionization.

The chromatographic profile (BPC, base peak chromatogram) of the Mo-4AR phytocomplex obtained by means of negative ionization is shown in FIG. 5.

The profile shows a dominant peak at 25 minutes of retention time. This peak corresponds to a compound with m/z 359. The retention time of this peak, its m/z value and its fragmentation spectrum (MS/MS) correspond to those of rosmarinic acid (commercial standard).

Figure 6:
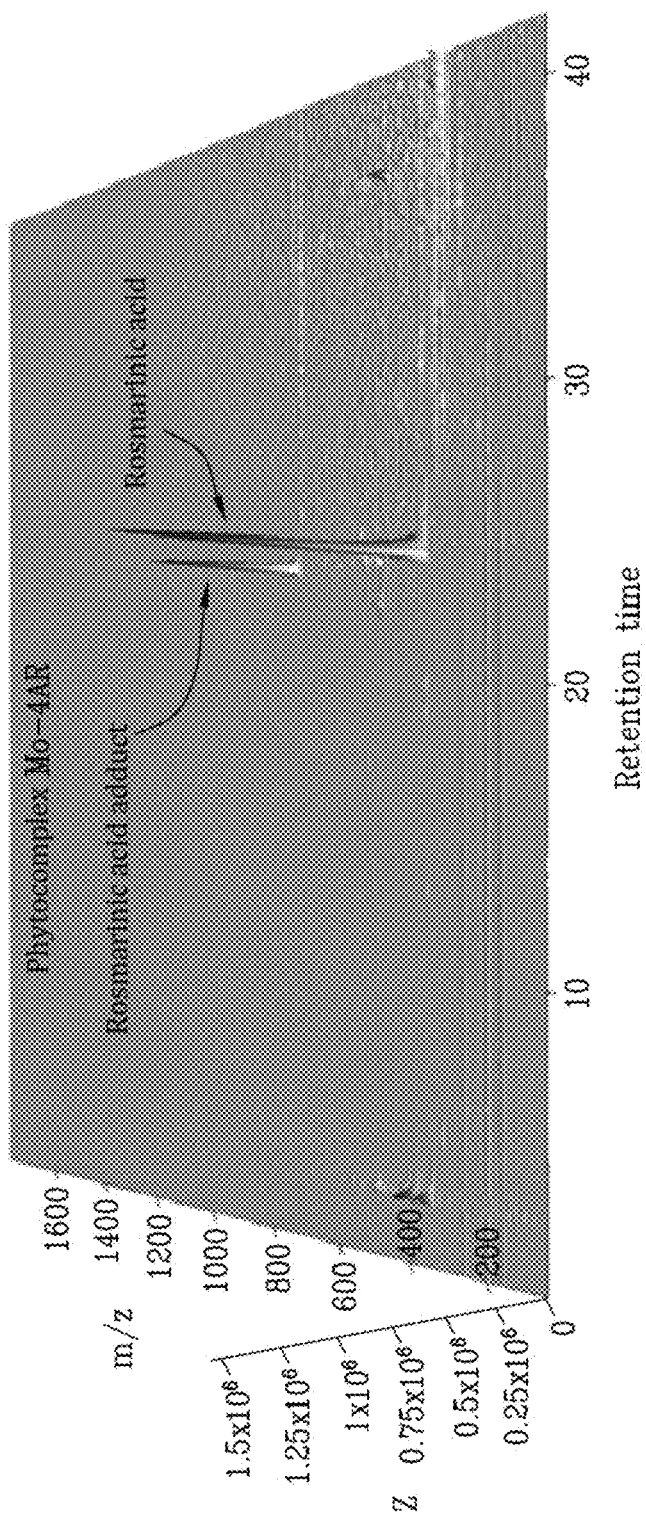
FIG. 6 shows the chromatogram, in three dimensions, of the Mo-4AR phytocomplex obtained by negative ionization.

FIG. 6 shows the chromatogram, in three dimensions, of the analyses conducted on the Mo-4AR phytocomplex with the negative ionization mode.

Figure 7:
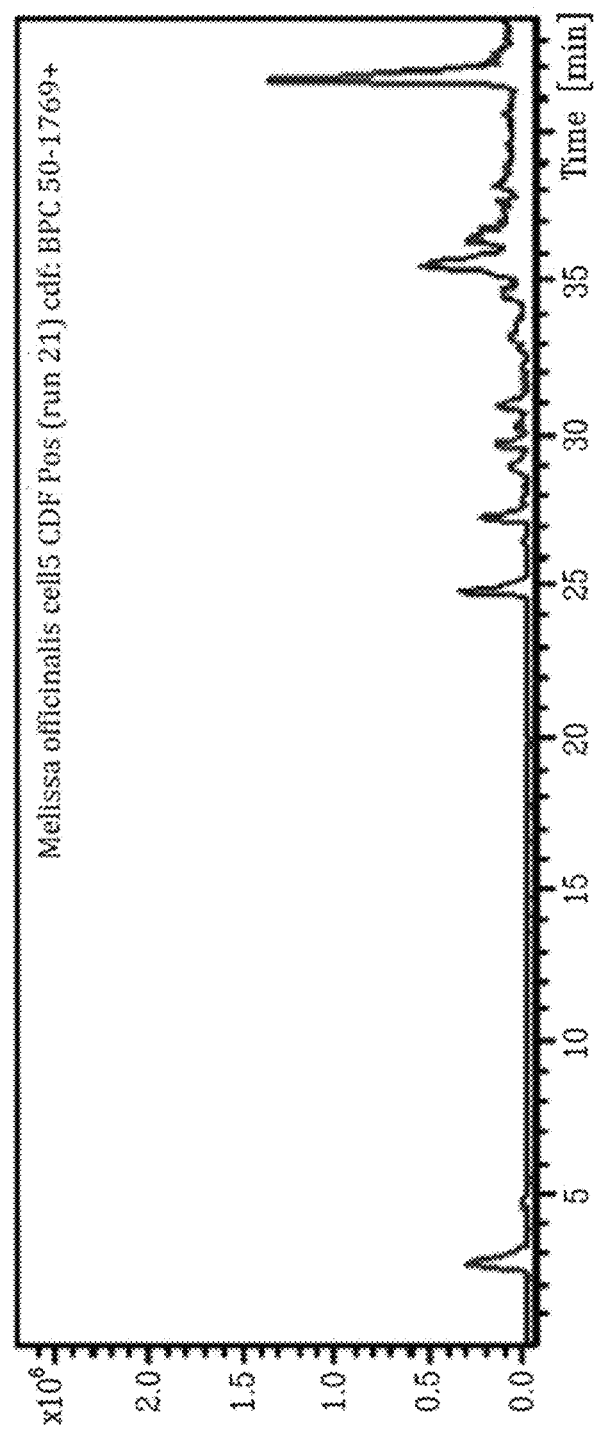
FIG. 7 shows the chromatographic profile of the Mo-4AR phytocomplex obtained by positive ionization.

The chromatographic profile (BPC, base peak chromatogram) of the Mo-4AR phytocomplex obtained by means of HPLC-ESI-MS in the positive ionization mode is shown in FIG. 7.

Figure 8:
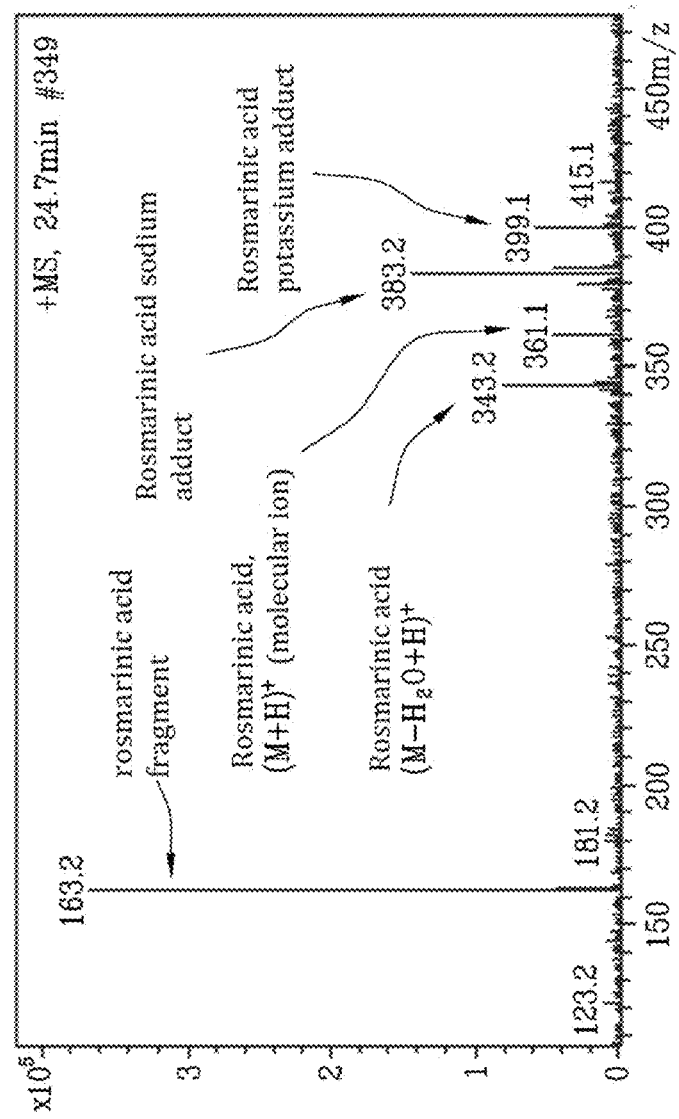
FIG. 8 shows the spectrum of the peak of rosmarinic acid in the positive ionization mode.

The peak for the rosmarinic acid is not very evident (indicated by the arrow) due to the low tendency of acids to become ionized. The spectrum of the peak in the positive ionization mode is shown in FIG. 8.

Figure 9:
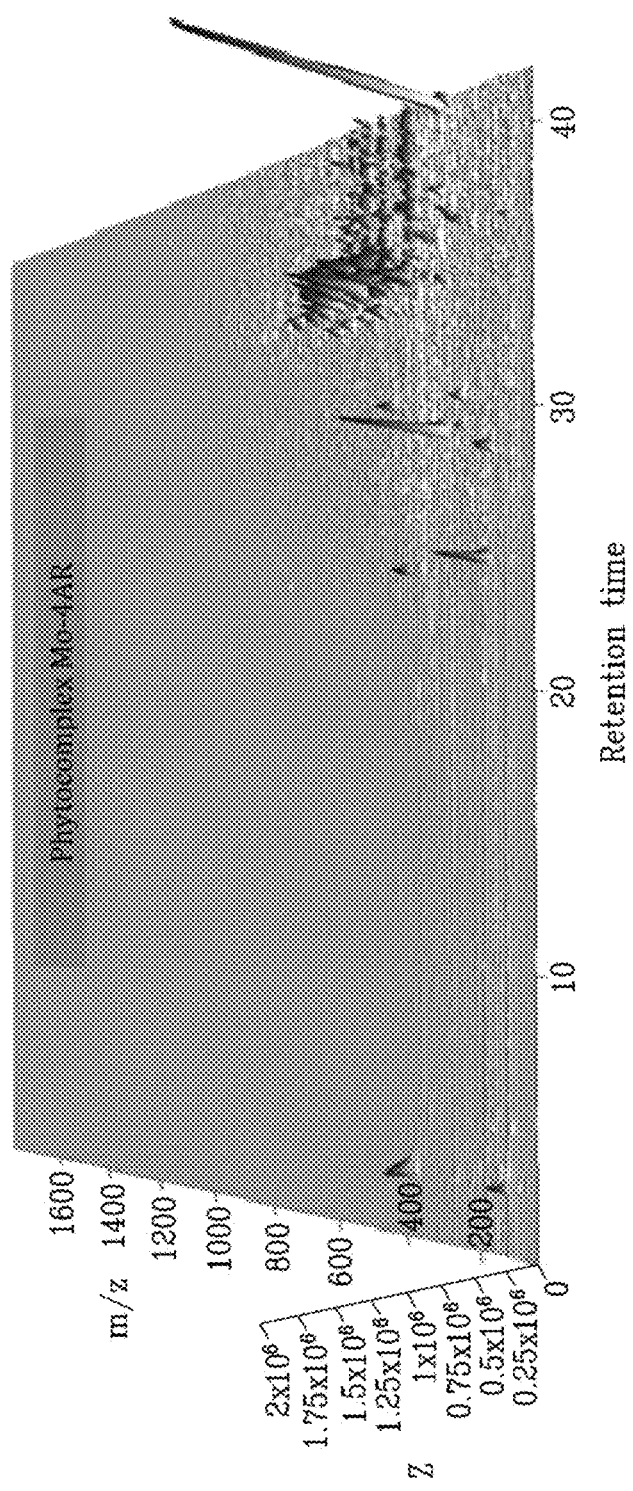
FIG. 9 shows the chromatogram, in three dimensions, of the Mo-4AR phytocomplex obtained by positive ionization.

FIG. 9 shows the chromatogram, in 3 dimensions, of the analysis of the Mo-4AR phytocomplex conducted in the positive ionization mode.

The matrix in the negative ionization mode comprises 30 signals (corresponding to metabolites and adducts and fragments thereof), the one in the positive mode comprises 70 signals (FIG. 10).

c) Quantitative analysis of polysaccharide content in the Mo-4AR phytocomplex

The analysis was conducted by adapting the phenol-sulphuric method (Segarra et al., 1995, Am J Enol Vitic.). This method entails an acid hydrolysis of the polysaccharides, which release monosaccharides. The monosaccharides react with the phenol, producing a yellow colour that can be measured with a spectrophotometer at 490 nm. The results obtained indicate an amount of polysaccharides equal to 500 mg/g of Mo-4AR phytocomplex, equivalent to 50%.

d) Analysis of the protein content of the Mo-4AR phytocomplex

A determination of the total content of protein nitrogen was conducted on the Mo-4AR phytocomplex using the Kjeldahl method, as described in Lynch, J M. et al., "Kjeldahl nitrogen analysis as a reference method for protein determination in dairy products" Journal of AOAC International (1999), 82(6), 1389-1398.

The protein content in the Mo-4AR phytocomplex was equal to 18% w/w.

e) Analysis of the lipid content of the Mo-4AR phytocomplex

The extraction of the total lipid fraction was carried out on the Mo-4AR phytocomplex by Soxhlet extraction with dichloromethane, extended for at least 12 hours according to the method described in Martinez M. et al., "Soxhlet lipids extraction from cotton from different producing areas. Comparison of dichloromethane or successive dichloromethane-methanol extractions". Grasas y Aceites (1997), 48 (4), 226-230. The lipid content in the Mo-4AR phytocomplex was equal to 8.5% w/w.

f) Analysis of the moisture and ash in the Mo-4AR phytocomplex

A determination of moisture was carried out on the phytocomplex by leaving the material in a stove at 40° C. for 12 hours. The determination of ash was obtained by treating the material in a muffle furnace at 300° C. until arriving at a constant weight. The moisture of the phytocomplex was equal to 2.5%, whilst the ash was equal to 4.5%.

Preparation of the Mo-4AR on an Industrial Scale

Meristematic cells, stabilized and selected as previously described, deriving from the line of *Melissa officinalis* called Mo-4AR, cultured in solid MO medium (Gamborg B5 containing 20 g/L of sucrose, 1 mg/L of naphthaleneacetic acid, 1 mg/L of indoleacetic acid, 0.5 mg/L of kinetin and 0.8% of plant agar, final pH 6.5) were inoculated into 10 flasks with a 1-litre capacity, containing 200 ml of liquid MO medium. The amount of meristematic cells inoculated into the liquid medium was equal to 6% W/V. The suspensions thus obtained were incubated in the dark at 25° C. and placed on top of an orbital shaker set on 120 RPM. After 7 days of incubation the cell suspensions were used to inoculate 10 flasks with a 3-litre capacity, containing 800 ml of liquid MO medium. 200 ml of the cell suspension was transferred into 800 ml of MO medium contained in a flask with a 3-litre capacity. The suspensions thus obtained were incubated in the dark at 25° C. and placed on top of an orbital shaker set on 120 RPM. After 7 days of incubation the cell suspensions were used to inoculate a bioreactor containing 90 litres of MO-F medium (Gamborg B5 with the addition of 35 g/L of sucrose, 0.5 mg/L of NAA, 0.5 mg/L of IAA, and 0.25 mg/L of K, final pH 6.5).

After 14 days of growth in the bioreactor the plant biomass (100 litres of cell suspension) was collected and filtered over a nylon mesh with a porosity of 50 μm and washed with 62 L of sterile saline solution (0.9% W/V). The washed cells (fresh weight 31 kg) were supplemented with 310 g of citric acid and homogenized with an Ultra-Turrax.

The homogenized cells were dried. 3120 g of Mo-4AR phytocomplex were obtained from 100 litres of cell suspension.

Test to Assess the Cytoprotective Activity of the Mo-4AR Phytocomplex on Macrophage Cells, after Oxidative Stress with LPS, by Determination of Autophagy, Mitochondrial Morphology, IL-1b Expression and Cytotoxicity on Macrophage Cell Cultures.

The test was performed on a THP-1 cell line. This cell line consists of monocytes derived from the peripheral blood of a patient with acute myeloid leukaemia. The THP-1 cells are differentiated into macrophages with PMA (phorbol 12-myristate 13-acetate). The cell line is maintained in suspension or adhesion. The macrophages are activated with LPS in the presence or absence of the extract of the Mo-4AR phytocomplex.

Phytocomplex extraction for setting up the biological assay: 100 mg of Mo-4AR phytocomplex, subsequently treated with 3 volumes of methanol, were weighed for the extraction. The solution obtained was mixed with a Vortex mixer and subjected to sonication in an ice bath for 15 minutes; it was subsequently centrifuged at 4500 rpm for 10 minutes at 4° C. The supernatant obtained was recovered and divided into 30 μL aliquots. The extraction solvent was then made to evaporate by means of a SpeedVac for 3 hours a room temperature. The dried samples were stored at −20° C. until use.

Shortly before administration to the cells (stimulated with 1 μg/mL LPS), an aliquot of dried sample (corresponding to 30 μL of extract) was solubilized in 200 μL of ethanol and 1800 μL of water. 500 μL of the dilution was added to 2.5 mL of RPMI 1640 medium, filtered at 0.22 μm to make it sterile. The resulting solution was used to incubate 20,000,000 THP-1 cells. The same number of THP-1 cells was incubated into 2.5 mL of RPMI medium supplemented with 500 μL of sterile water as a control sample. The samples of treated cells and samples treated with the control solution were incubated for 18 hours at 37° C. and with a 5% $CO_2$ flow (V/V). At the end of incubation, cells washed with serum-free RPMI were used for the test to evaluate autophagy, mitochondrial morphology, IL-1β and LDH.

Evaluation of Autophagy Via LC3 Expression

Cells treated and not treated with the phytocomplex were fixed on a slide, stained with anti-LC3 antibody (a marker of autophagosomic vesicles) and the autophagic activity was measured under the various conditions. An evaluation of the degree of autophagy is carried out by counting the number of autophagic cells (fluorescent) present within the cells using a fluorescence microscope.

Figure 11:
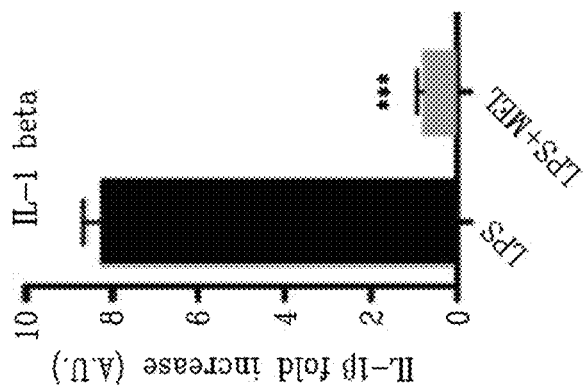
FIG. 11 shows an evaluation of the number of autophagosomic vesicles present inside the cells marked with the anti-LC3 antibody in THP-1 cells stimulated with LPS and treated with the Mo-4AR phytocomplex.

Marking with the anti-LC3 antibody showed that the Mo-4AR phytocomplex of *Melissa officinalis* is capable of significantly inhibiting the production of autophagosomes in THP-1 cells after the induction of oxidative stress with LPS (FIG. 11, $p<0.01$, *$p<0.001$ with one-way ANOVA and Dunnett's post-hoc test). Autophagy is a cell defence mechanism that generally increases when the cell is in a situation of stress. Its activation is not a negative process per se, but it indicates that the cell is responding to an insult that is potentially damaging it. The Mo-4AR phytocomplex significantly reduces autophagy in THP-1 cells after oxidative stress, thus making the induction of stress by LPS less effective.

Evaluation of Mitochondrial Morphology

An evaluation of mitochondrial morphology was carried out using a fluorescent stain specific for the mitochondrial protein TOM20 (immunofluorescence). The shape of mitochondria is a good indicator of their health; in particular, the ratio between the major and minor axes ("aspect ratio", AR). The higher the AR, the better and healthier the mitochondria: therefore, a higher value corresponds to a positive result with respect to cell protection.

Figure 12:
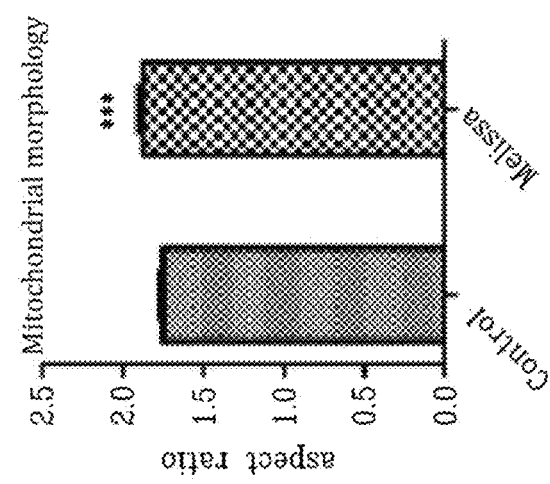
FIG. 12 shows an evaluation of mitochondrial morphology on THP-1 cells stimulated with LPS, treated and not treated with the Mo-4AR phytocomplex.

The evaluation of the mitochondrial morphology was carried out on THP-1 cells stimulated with LPS, treated and not treated with the MO-4AR phytocomplex (FIG. 12, ***p<0.001 with one-way ANOVA and Dunnett's post-hoc test).

The Mo-4AR phytocomplex obtained from meristematic cells of *Melissa officinalis* demonstrated to be effective in increasing the "aspect ratio" (ratio between the major axis and the minor axis of a mitochondrion considered as approximately an ellipse) of the mitochondria compared to the control.

Evaluation of IL-1β Expression

Il-1β is a pro-inflammatory cytokine and was determined by RT-PCR analysis. The nucleic acids of the THP-1 cells, treated and not treated with Mo-4AR phytocomplex and LPS for 18 hours, were extracted using a specific lysis buffer and an RNA-kit. A cDNA transcription kit was used to synthesize cDNA from the extracted RNA. A Fast Real Time PCR instrument was used to study the gene expression of IL-1β.

Figure 13:
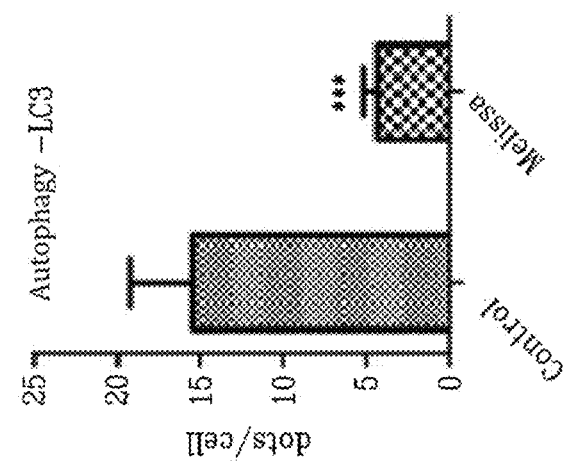
FIG. 13 shows the expression of IL-1β in THP-1 cells stimulated with LPS and treated with the Mo-4AR phytocomplex.

The Mo-4AR phytocomplex obtained from meristematic cells of *Melissa officinalis* demonstrated to be effective in inhibiting the expression of IL-1β in THP-1 cells stimulated with LPS (FIG. 13, ***p<0.001 with one-way ANOVA and Dunnett's post-hoc test).

Evaluation of Cytotoxicity (LDH)

Figure 14:
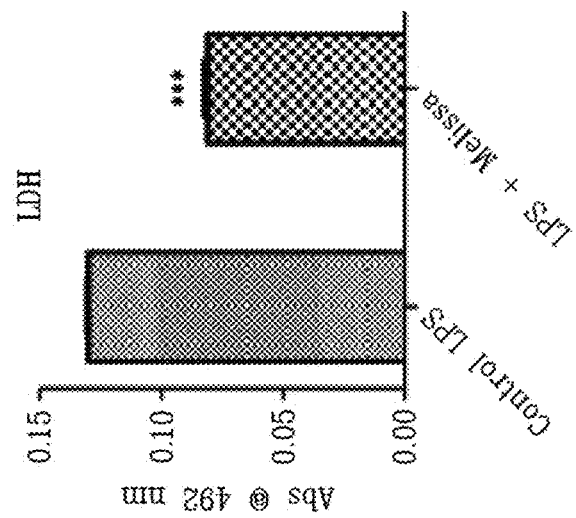
FIG. 14 shows an evaluation of cytotoxicity with the LDH test in THP-1 cells stimulated with LPS, treated and not treated with the Mo-4AR phytocomplex.

An evaluation of cytotoxicity in THP-1 cells, treated and not treated with Mo-4AR phytocomplex from *Melissa officinalis* and LPS, was carried out by quantifying the enzyme lactic dehydrogenase (LDH), which is freed in the culture medium after cell lysis. After 18 hours of incubation, an aliquot of the medium is drawn and incubated with Lactate Dehydrogenase Assay Mixture. The solution is added in a 2:1 ratio to the medium to be assayed. The solution is incubated in the dark at room temperature for 20 minutes. The reaction is interrupted by adding HCl 1 N. The samples are read with a spectrophotometer, by measuring absorbance at 490 nm. The Mo-4AR phytocomplex obtained from meristematic cells of *Melissa officinalis* demonstrated to be effective in limiting cell death caused by LPS (FIG. 14, ***p<0.001 with one-way ANOVA and Dunnett's post-hoc test).

Evaluation of the Effect of the Mo-4AR Phytocomplex on a Cellular Model of Parkinson's Disease Parkinson's disease is a neurodegenerative pathology that affects 1% of the population aged over 60 and which, from a cellular standpoint, involves dopaminergic neurons of the substantia nigra of the mesencephalon. Neuron death leads to a hypokinetic-rigid syndrome or paralysis agitans. In this biological test, use was made of an in vitro model of dopaminergic neurons (LUHMES), which were exposed to a neurotoxin (rotenone) to simulate damage that could mimic what occurs in patients with Parkinson's disease. The Mo-4AR phytocomplex from meristematic cells of *Melissa officinalis* was used to evaluate a protective effect vis-à-vis damaged neurons.

The Mo-4AR phytocomplex was extracted with methanol as described in the previous paragraph. The extract obtained was filtered and lyophilized before use. The lyophilizate obtained was added directly to the culture medium (at a final concentration corresponding to 0.5 mg/mL of phytocomplex).

Cell Toxicity Test

Under one condition, cells were subjected to a neurotoxic environment by treating them with rotenone 5 nM at pH=6 for 2 hours (positive control) whilst under another condition the rotenone was added together with the extract of the Mo-4AR phytocomplex in order to verify its possible protective effect on the cells. At the end of 2 hours of incubation at 37° C. and with a 5% $CO_2$ flow (V/V), assays were performed on the enzyme lactic dehydrogenase (LDH) in the culture media under the two different culture conditions.

Figure 15:
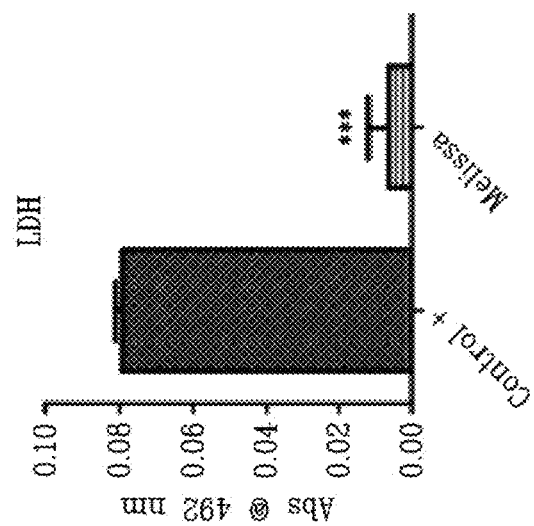
FIG. 15 shows an evaluation of cytotoxicity with the LDH test in dopaminergic neurons (LUHMES) treated with rotenone, with and without treatment with the Mo-4AR phytocomplex.

As may be noted from FIG. 15, the effect of the Mo-4AR phytocomplex obtained from meristematic cells of *Melissa officinalis* is significantly positive. In other words, the Mo-4AR phytocomplex protects dopaminergic neurons against the damage induced by rotenone (***p<0.001 with one-way ANOVA and Dunnett's post-hoc test).

Evaluation of LC3 Autophagy

Figure 16:
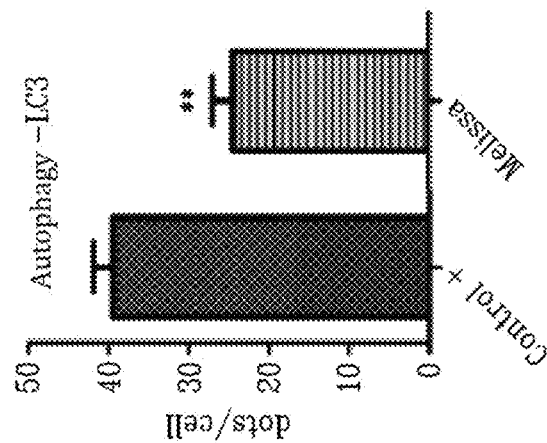
FIG. 16 shows an evaluation of the number of autophagosomic vesicles present within dopaminergic neurons (LUHMES) treated with rotenone, with and without treatment with the Mo-4AR phytocomplex.

In order to study the mechanism whereby the phytocomplex reduces the cell death of dopaminergic neurons, the cells were damaged in the same way to study toxicity (rotenone 5 nM at pH=6 for 2 hours) in the presence or absence of the Mo-4AR phytocomplex. The cells were then fixed on the slide, stained with anti-LC3 antibody (a marker of autophagosomic vesicles) and the autophagic activity was quantified under the two different conditions (FIG. 16, **p<0.01 with one-way ANOVA and Dunnett's post-hoc test).

In the LC3 staining of dopaminergic neurons, one can note that, in the cells treated with the Mo-4AR phytocomplex of *Melissa officinalis*, the intensity of the colour (white) is less than that of cells not treated with the phytocomplex (+control) (FIG. 17).

Evaluation of Mitochondrial Morphology

The mechanism of action of rotenone consists in blocking cellular respiration at the mitochondrial level (blocking of the respiratory chain). It therefore prevents the cell from producing energy in the form of ATP using oxygen. This process takes place in the mitochondria and the morphology of the mitochondria was analysed (again under the previously described conditions) by staining of the mitochondrial protein TOM20 to investigate the mechanism of protection exerted by the Mo-4AR phytocomplex. The shape of mitochondria is an indicator of their health. In particular, the ratio between the major and minor axes ("aspect ratio") was measured.

The Mo-4AR phytocomplex from meristematic cells of *Melissa officinalis* demonstrated to be capable of significantly increasing the mitochondrial aspect ratio in dopaminergic neurons treated with rotenone (FIG. 18, **p<0.01 with one-way ANOVA and Dunnett's post-hoc test).

In conclusion, the application of the Mo-4AR phytocomplex obtained from meristematic cells of *Melissa officinalis* to a model of Parkinson's disease consisting of dopaminergic neurons damaged with rotenone lends protection to cells against the damage induced by the rotenone itself.

Formulation of the Mo-4AR Phytocomplex in Two-Phase and Multiple Emulsions and in Gel Form The Mo-4AR phytocomplex was dispersed in glycerine in a concentration of 3% W/W (INCI NAME: Glycerin (and) *Melissa Officinalis* Callus Lysate (and) Citric Acid). The dispersion was added at 3% to the formulas described below.

TABLE 4

Emulsions (two-phase and multiple O/A, A/O, A/S, A/O/A)

| Ingredients | % |
|---|---|
| Water | 60-95 |
| Rheology modifiers of the aqueous phase (polysaccharides, proteins, synthetic polymers, inorganic polymers) | 0.1-3 |
| Emollient lipids (natural oils and butters, synthetic lipids, silicones) | 1-30 |
| Natural and synthetic waxes | 0-10 |
| Emulsifier (ionic, non-ionic, silicone, polymeric) | 0.1-5 |
| Fatty alcohols | 0-5 |
| Preservative system | 0-2 |
| Glycerin (and) Melissa Officinalis Callus Lysate (and) Citric Acid | 3 |

TABLE 5

Gel formulations

| Ingredients | % |
|---|---|
| Water | 70-98 |
| Humectants | 0-20 |
| Rheology modifiers (polysaccharides, proteins, synthetic polymers, inorganic polymers) | 0.1-20 |
| Emollient lipids (natural oils and butters, synthetic lipids, silicones) | 0-10 |
| Emulsifiers (ionic, non-ionic, silicone, polymeric) | 0-2 |
| Conditioning agents (protein hydrolysates, amino acids, quaternary polymers) | 0-5 |
| Preservative system | 0-2 |
| Glycerin (and) Melissa Officinalis Callus Lysate (and) Citric Acid | 3 |

The components of the aqueous phase were mixed and heated to 70° C. The components of the oily phase were mixed and heated to 75° C. The two phases were combined under the action of a turbo emulsifier. After cooling to about 40° C., the Mo-4AR phytocomplex dispersed in glycerine was added under gentle stirring.

The invention claimed is:

1. A meristematic cell line derived from a plant belonging to the genus *Melissa*, obtained by means of a process comprising the steps of:
   1) plating a tissue obtained from a plant belonging to the genus *Melissa* onto a solid culture medium;
   2) isolating a plurality of cellular clones;
   3) inoculating each of the isolated clones into a liquid culture medium;
   4) determining the rosmarinic acid and polysaccharide content for each clone;
   5) selecting a cellular clone with the highest rosmarinic acid and polysaccharide content, wherein the solid and liquid culture media comprise salts suitable for the growth of plant cells, sucrose, naphthylacetic acid (NAA), indoleacetic acid (IAA) and kinetin, and
   wherein said cell line comprises an amount of rosmarinic acid greater than 0.05% w/w, and an amount of polysaccharides from 25% to 70% w/w relative to the dry mass of the cell line.

2. The meristematic cell line according to claim 1, wherein the solid and liquid culture media each comprise sucrose in a concentration from 15 to 50 g/L, NAA in a concentration from 0.1 to 2.5 mg/L, indoleacetic acid (IAA) in a concentration from 0.1 to 2.5 mg/L, and kinetin in a concentration from 0.1 mg/L to 2 mg/L.

3. The meristematic cell line according to claim 1, wherein the liquid culture medium comprises: sucrosein a concentration of from 25 to 50 g/L, indoleacetic acid (IAA) in a concentration of from 0.1 to 2 mg/L, and kinetin in a concentration of from 0.2 mg/L to 1 mg/L.

4. The meristematic cell line according to claim 1, wherein the solid culture medium comprises: sucrosein a concentration of from 10 to 30 g/L, naphthaleneacetic acid (NAA) in a concentration of from 0.1 to 2 mg/L, indoleacetic acid (IAA) in a concentration of from 0.1 to 2 mg/L, and kinetin in a concentration of from 0.2 mg/L to 1 mg/L.

5. The meristematic cell line according to claim 1, wherein the salts suitable for the growth of plant cells are selected from the group consisting of: $CaCl_2$, $KNO_3$, $MgSO_4$, $NaH_2PO_4$, $(NH_4)_2SO_4$ and combinations thereof.

6. The meristematic cell line according to claim 1, wherein the salts suitable for the growth of plant cells are selected from the group consisting of: $CoCl_2.6H_2O$, $CuSO_4.5H_2O$, $NaEDTA.2H_2O$, $FeSO_4.7H_2O$, $H_3BO_3$, KI, $MnSO_4H_2O$, $Na_2MoO_4.2H_2O$, $ZnSO_4.7H_2O$ and combinations thereof.

7. The meristematic cell line according to claim 5, wherein the solid and liquid culture media each comprise $CaCl$ in a concentration from 120 to 170 mg/L, $KNO_3$ in a concentration from 800 to 3000 mg/L, $MgSO_4$ in a concentration from 220 to 270 mg/L, $NaH_2PO_4$ in a concentration from 100 to 180 mg/L, and $(NH_4)_2SO_4$ in a concentration from 100 to 180 mg/L.

8. The meristematic cell line according to claim 6, wherein the solid and liquid culture media each comprise $CoCl_2.6H_2O$ in a concentration comprising 0.01 to 0.05 mg/L, $CuSO_4.5H_2O$ in a concentration comprising 0.01 to 0.05 mg/L; $NaEDTA. 2H_2O$ in a concentration from 20 to 60 mg/L, $FeSO_4.7H_2O$ in a concentration comprising 15 to 45 mg/L; $H_3BO_3$ in a concentration comprising 1 to 7 mg/L; KI in a concentration from 0.1 to 2 mg/L; $MnSO_4.H_2O$ in a concentration comprising 5 to 20 mg/L; $Na_2MoO_4.2H_2O$ in a concentration comprising 0.1 to 0.5 mg/L, and $ZnSO_4.7H_2O$ in a concentration comprising 0.5 to 5 mg/L.

9. The meristematic cell line according to claim 1, wherein both the solid and liquid culture media comprise vitamins suitable for the growth of plant cells selected from the group consisting of: myo-inositol, nicotinicacid, pyridoxine-HCl, thiamine-HCl and combinations thereof.

10. The meristematic cell line according to claim 9, wherein myo- inositol is present in a concentration from 70 to 130 mg; pyridoxine-HCl is present in a concentration from 70 to 130 mg, and thiamine-HCl is present in a concentration from 5 to 20 mg/L.

11. The meristematic cell line according to claim 1, comprising an amount of polysaccharides from 30% to 65% w/w.

12. The meristematic cell line according claim 1, comprising an amount of proteins from 1% to 35% w/w.

13. The meristematic cell line according to claim 1, comprising an amount of lipids from 5% to 25% w/w.

14. A meristematic cell line according to claim 1, wherein the plant belongs to species *Melissa officinalis*.

15. A meristematic cell line according to claim 1, wherein the rosmarinic acid is from 0.05% to 40% w/w.

16. A phytocomplex or an extract of the meristematic cell line according to claim 1.

17. A phytocomplex according to claim 16, which consists of dried or lyophilized cells, or a cellular homogenate, or cell walls and the components thereof.

18. A phytocomplex according to claim 16, which is a cellular homogenate comprising an amount of rosmarinic acid greater than 0.05% w/w, relative to the dry mass of the phytocomplex.

19. A composition comprising the meristematic cell line according to claim 1.

20. The composition according to claim 19, comprising the meristematic cell line and/or the phytocomplex and/or the extract in a concentration from 0.01% to 30% w/w, relative to the total composition.

21. The composition according to claim 20, wherein said phytocomplex is a cellular homogenate.

22. The composition according to claim 19, formulated as a cream, gel cream, gel, serum, oil, emulsion, emulsion gel (emulgel), ointment, eye drops, mouthwash, patch, spray, preferably formulated as a nasal spray, stick, pill, capsule, tablet, granular powder, hard-shelled capsule, orally dissolving granule, sachet, lozenge, liposome, or sterile solution, or suspension.

23. A process for the preparation and selection of plant meristematic cells derived from a plant belonging to genus *Melissa*, said cells comprising an amount of rosmarinic acid greater than 0.05% w/w, and an amount of polysaccharides from 25% to 70% w/w relative to the dry mass of the cell line, said process comprising the steps of:
1) plating a tissue obtained from a plant of the genus *Melissa* onto a solid culture medium;
2) isolating a plurality of cellular clones;
3) inoculating each of the isolated clones into a liquid culture medium;
4) determining the rosmarinic acid and polysaccharide content for each clone;
5) selecting a cellular clone with the highest rosmarinic acid and polysaccharide content,
wherein the solid and liquid culture media comprise salts suitable for the growth of plant cells, sucrose, naphthylacetic acid (NAA), indoleacetic acid (IAA) and kinetin.

* * * * *